United States Patent
Bae et al.

(10) Patent No.: US 8,349,015 B2
(45) Date of Patent: Jan. 8, 2013

(54) INTERVERTEBRAL IMPLANT WITH INTEGRATED FIXATION

(75) Inventors: Hyun W. Bae, Santa Monica, CA (US);
Nicholas Slater, Chandler, AZ (US);
Joshua A Butters, Chandler, AZ (US);
Daniel F. Justin, Logan, UT (US);
Dylan M. Hushka, Chandler, AZ (US);
Rick Delamarter, Los Angeles, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 292 days.

(21) Appl. No.: 12/640,816

(22) Filed: Dec. 17, 2009

(65) Prior Publication Data
US 2010/0204796 A1    Aug. 12, 2010

Related U.S. Application Data

(60) Provisional application No. 61/151,701, filed on Feb. 11, 2009, provisional application No. 61/232,705, filed on Aug. 10, 2009, provisional application No. 61/232,745, filed on Aug. 10, 2009, provisional application No. 61/257,734, filed on Nov. 3, 2009, provisional application No. 61/257,667, filed on Nov. 3, 2009.

(51) Int. Cl.
*A61F 2/44*    (2006.01)
(52) U.S. Cl. ................................... 623/17.16
(58) Field of Classification Search .............. 606/60, 606/246–279; 623/17.11–17.16
See application file for complete search history.

(56) References Cited

U.S. PATENT DOCUMENTS

| | | | |
|---|---|---|---|
| 3,486,505 A | 12/1969 | Morrison |
| 4,047,524 A | 9/1977 | Hall |
| 4,501,269 A | 2/1985 | Bagby |
| 4,820,305 A | 4/1989 | Harms et al. |
| 4,834,757 A | 5/1989 | Brantigan |
| 4,946,378 A | 8/1990 | Hirayama et al. |
| 5,192,327 A | 3/1993 | Brantigan |
| 5,306,309 A | 4/1994 | Wagner |
| 5,314,477 A | 5/1994 | Marnay |

(Continued)

FOREIGN PATENT DOCUMENTS
EP    179695 A1    4/1986
(Continued)

OTHER PUBLICATIONS
International Search Report and Written Opinion, PCT/US2010/22494, dated Oct. 25, 2010.
(Continued)

*Primary Examiner* — Kevin T Truong
*Assistant Examiner* — Christopher Beccia
(74) *Attorney, Agent, or Firm* — Lerner, David, Littenberg, Krumholz & Mentlik, LLP

(57) ABSTRACT

A system for spinal surgery includes a prosthesis comprising a plurality of bone anchors which engage an intervertebral construct for fusion or motion preservation. The fusion construct comprises a spacer optionally encircled by a jacket. The motion preservation construct may comprise an articulating disc assembly or an elastomeric disc assembly. Any of the constructs may occupy the intervertebral disc space between adjacent vertebrae after removal of an intervertebral disc. The anchors slidingly engage the construct to securely fix the prosthesis to the vertebrae. The anchors and jacket of the fusion construct provide a continuous load path across opposite sides of the prosthesis so as to resist antagonistic motions of the spine.

29 Claims, 27 Drawing Sheets

U.S. PATENT DOCUMENTS

| | | | |
|---|---|---|---|
| 5,431,658 A | | 7/1995 | Moskovich |
| 5,443,515 A | | 8/1995 | Cohen et al. |
| 5,507,816 A | | 4/1996 | Bullivant |
| 5,514,180 A | | 5/1996 | Heggeness |
| 5,609,635 A | | 3/1997 | Michelson |
| 5,683,394 A | | 11/1997 | Rinner |
| 5,702,449 A | | 12/1997 | McKay |
| 5,709,683 A | | 1/1998 | Bagby |
| 5,713,899 A | | 2/1998 | Marnay et al. |
| 5,893,889 A | * | 4/1999 | Harrington ................ 623/17.16 |
| 6,039,762 A | | 3/2000 | McKay |
| 6,096,080 A | | 8/2000 | Nicholson et al. |
| 6,113,638 A | | 9/2000 | Williams et al. |
| 6,120,503 A | | 9/2000 | Michelson |
| 6,235,059 B1 | | 5/2001 | Benezech et al. |
| 6,241,769 B1 | | 6/2001 | Nicholson |
| 6,325,805 B1 | | 12/2001 | Ogilvie et al. |
| 6,336,928 B1 | | 1/2002 | Guerin et al. |
| 6,364,880 B1 | | 4/2002 | Michelson |
| 6,432,107 B1 | | 8/2002 | Ferree |
| 6,447,524 B1 | | 9/2002 | Knodel et al. |
| 6,447,546 B1 | | 9/2002 | Bramlet et al. |
| 6,582,468 B1 | | 6/2003 | Gauchet |
| 6,679,887 B2 | | 1/2004 | Nicholson et al. |
| 6,716,245 B2 | | 4/2004 | Pasquet et al. |
| 6,726,720 B2 | * | 4/2004 | Ross et al. ................ 623/17.13 |
| 6,740,118 B2 | | 5/2004 | Eisermann et al. |
| 6,743,256 B2 | | 6/2004 | Mason |
| 6,800,093 B2 | | 10/2004 | Nicholson |
| 7,048,766 B2 | | 5/2006 | Ferree |
| 7,056,344 B2 | | 6/2006 | Huppert et al. |
| 7,056,345 B2 | | 6/2006 | Kuslich |
| 7,060,097 B2 | | 6/2006 | Fraser et al. |
| 7,128,761 B2 | | 10/2006 | Kuras et al. |
| 7,204,852 B2 | | 4/2007 | Marnay et al. |
| 7,235,101 B2 | | 6/2007 | Berry et al. |
| 7,320,707 B2 | | 1/2008 | Zucherman et al. |
| 7,331,995 B2 | | 2/2008 | Eisermann et al. |
| 7,364,589 B2 | | 4/2008 | Eisermann |
| 7,503,934 B2 | | 3/2009 | Eisermann et al. |
| 7,503,935 B2 | | 3/2009 | Zucherman et al. |
| 7,588,600 B2 | | 9/2009 | Benzel et al. |
| 7,594,931 B2 | | 9/2009 | Louis et al. |
| 7,611,538 B2 | * | 11/2009 | Belliard et al. ............ 623/17.15 |
| 7,658,766 B2 | | 2/2010 | Melkent et al. |
| 7,695,516 B2 | * | 4/2010 | Zeegers ..................... 623/17.14 |
| 7,749,271 B2 | | 7/2010 | Fischer et al. |
| 7,763,076 B2 | * | 7/2010 | Navarro et al. ............ 623/17.15 |
| 7,896,919 B2 | * | 3/2011 | Belliard et al. ............ 623/17.15 |
| 8,021,403 B2 | | 9/2011 | Wall et al. |
| 8,034,076 B2 | | 10/2011 | Criscuolo et al. |
| 8,100,974 B2 | * | 1/2012 | Duggal et al. ............ 623/17.15 |
| 2002/0035400 A1 | * | 3/2002 | Bryan et al. ............ 623/17.15 |
| 2002/0165613 A1 | | 11/2002 | Lin |
| 2003/0045940 A1 | | 3/2003 | Eberlein et al. |
| 2003/0195517 A1 | | 10/2003 | Michelson |
| 2003/0195632 A1 | | 10/2003 | Foley et al. |
| 2004/0148028 A1 | | 7/2004 | Ferree et al. |
| 2004/0176853 A1 | | 9/2004 | Sennett |
| 2004/0199254 A1 | | 10/2004 | Louis et al. |
| 2004/0220668 A1 | | 11/2004 | Eisermann et al. |
| 2004/0220670 A1 | | 11/2004 | Eisermann et al. |
| 2004/0230307 A1 | | 11/2004 | Eisermann |
| 2004/0260286 A1 | * | 12/2004 | Ferree ............................. 606/61 |
| 2005/0004672 A1 | | 1/2005 | Pafford et al. |
| 2005/0043802 A1 | * | 2/2005 | Eisermann et al. ........ 623/17.16 |
| 2005/0149192 A1 | * | 7/2005 | Zucherman et al. ........ 623/17.11 |
| 2005/0149193 A1 | | 7/2005 | Zucherman et al. |
| 2005/0165408 A1 | | 7/2005 | Puno et al. |
| 2005/0192586 A1 | | 9/2005 | Zucherman et al. |
| 2006/0004453 A1 | | 1/2006 | Bartish et al. |
| 2006/0085071 A1 | | 4/2006 | Lechmann et al. |
| 2006/0116769 A1 | | 6/2006 | Marnay et al. |
| 2006/0129238 A1 | | 6/2006 | Paltzer |
| 2006/0136063 A1 | * | 6/2006 | Zeegers ..................... 623/17.14 |
| 2006/0178745 A1 | | 8/2006 | Bartish et al. |
| 2006/0212121 A1 | | 9/2006 | Ferree |
| 2007/0050032 A1 | | 3/2007 | Gittings et al. |
| 2007/0050033 A1 | | 3/2007 | Reo et al. |
| 2007/0118145 A1 | | 5/2007 | Fischer et al. |
| 2007/0233244 A1 | | 10/2007 | Lopez et al. |
| 2007/0233261 A1 | | 10/2007 | Lopez et al. |
| 2008/0015702 A1 | | 1/2008 | Lakin et al. |
| 2008/0051901 A1 | | 2/2008 | de Villiers et al. |
| 2008/0051902 A1 | | 2/2008 | Dwyer |
| 2008/0154377 A1 | | 6/2008 | Voellmicke |
| 2008/0249575 A1 | | 10/2008 | Waugh et al. |
| 2009/0005870 A1 | | 1/2009 | Hawkins et al. |
| 2009/0088849 A1 | | 4/2009 | Armstrong et al. |
| 2009/0164020 A1 | | 6/2009 | Janowski et al. |
| 2010/0004747 A1 | | 1/2010 | Lin |
| 2010/0185292 A1 | | 7/2010 | Hochschuler et al. |

FOREIGN PATENT DOCUMENTS

| | | |
|---|---|---|
| EP | 1327423 | 7/2003 |
| EP | 1790298 A1 | 5/2007 |
| EP | 1872746 | 1/2008 |
| WO | 03/039400 A2 | 5/2003 |
| WO | WO03053290 | 7/2003 |
| WO | 03092507 A2 | 11/2003 |
| WO | WO2004071359 | 8/2004 |
| WO | WO2004080355 | 9/2004 |
| WO | WO2004108015 | 12/2004 |
| WO | 2005051243 A2 | 6/2005 |
| WO | 2006051547 A2 | 5/2006 |
| WO | WO2006074414 | 7/2006 |
| WO | WO2006086494 | 8/2006 |
| WO | WO2007087366 | 8/2007 |
| WO | 2008/014453 A2 | 1/2008 |
| WO | WO2008021955 | 2/2008 |

OTHER PUBLICATIONS

International Search Report and Writen Opinion, PCT/US2010/044988, Dated Feb. 4, 2011.

International Search Report and Written Opinion for Application No. PCT/US2010/055259, dated Apr. 7, 2011.

European Search Report dated Sep. 26, 2012 for PCT/US2010022494.

* cited by examiner

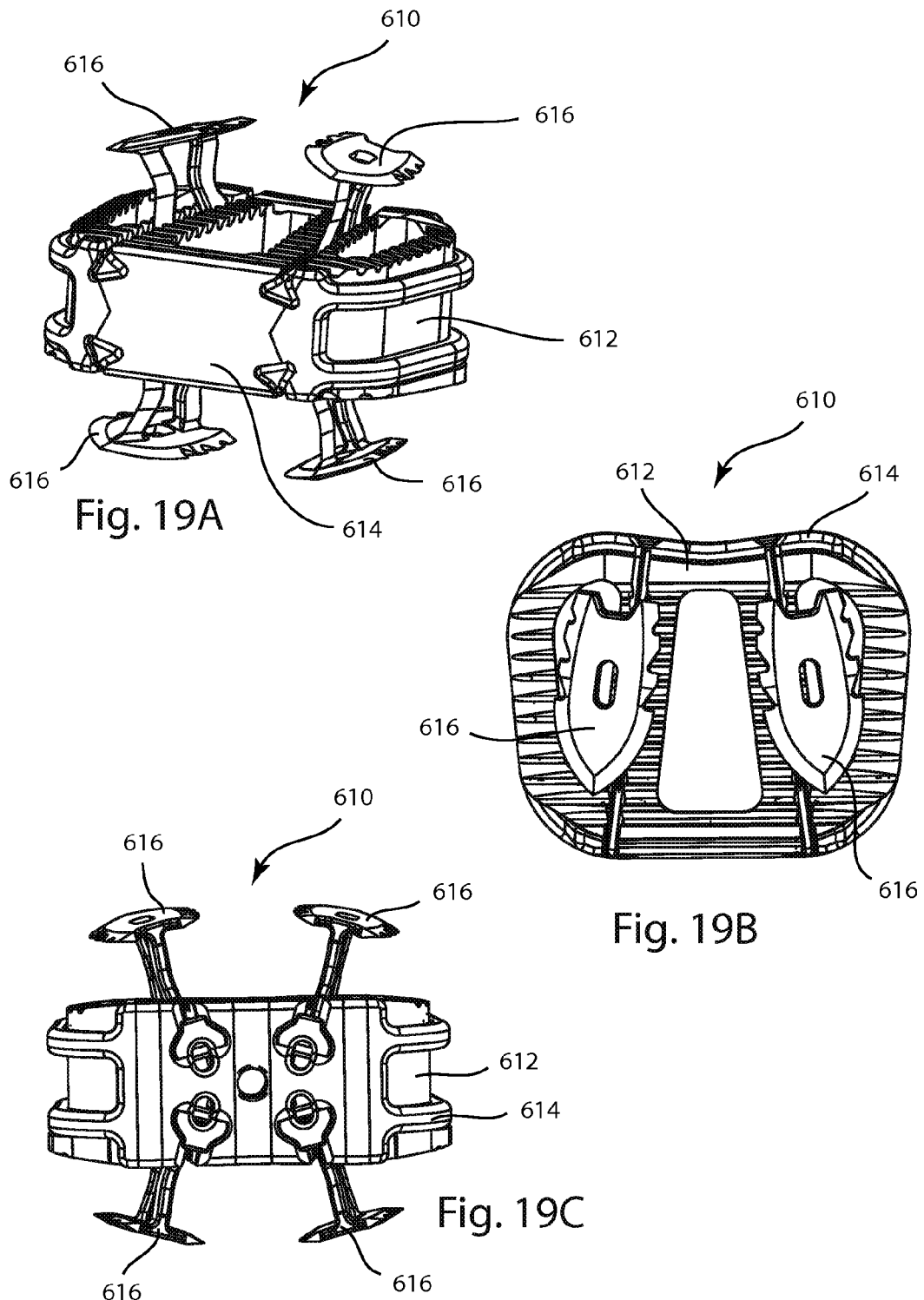

INTERVERTEBRAL IMPLANT WITH INTEGRATED FIXATION

CROSS-REFERENCE TO RELATED APPLICATIONS

This application claims the benefit of:

U.S. Application No. 61/151,701, filed Feb. 11, 2009, entitled INTERVERTEBRAL IMPLANT WITH INTEGRATED FIXATION, which is pending;

U.S. Application No. 61/232,705, filed Aug. 10, 2009, entitled INTERVERTEBRAL IMPLANT WITH INTEGRATED FIXATION, which is pending;

U.S. Application No. 61/232,745, filed Aug. 10, 2009, entitled INTERVERTEBRAL, which is pending;

U.S. Application No. 61/257,734, filed Nov. 3, 2009, entitled INTERVERTEBRAL IMPLANT WITH INTEGRATED FIXATION INCLUDING AN INSTRUMENT FOR IMPLANT REVISION, which is pending; and U.S. Application No. 61/257,667, filed Nov. 3, 2009, entitled INTERVERTEBRAL IMPLANT WITH INTEGRATED FIXATION, which is pending.

All of the above-referenced documents are hereby incorporated by reference in their entirety.

BACKGROUND OF THE INVENTION

The Field of the Invention

The invention relates to spinal surgery. More precisely, the present invention relates to intervertebral prostheses implanted following at least partial disc excision.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 19A (BAE-5 PROV) is a postero-lateral view of an alternate embodiment of an intervertebral fusion prosthesis; FIG. 19B is a caudal view of the intervertebral fusion prosthesis of FIG. 19A; and FIG. 19C is an anterior view of the intervertebral fusion prosthesis of FIG. 19A;

DETAILED DESCRIPTION

The present invention advances the state of the art by providing intervertebral prostheses with anchors to secure the prostheses to bone.

In this specification, the following terms are used with the specified definitions.

Antagonistic spinal motion is defined as substantially identical spinal motions in opposite directions. Therefore, spinal flexion and extension is an example of antagonistic spinal motions. Other examples include right and left axial rotation, right and left lateral bending, and anterior and posterior translation. In this specification, antagonistic spinal motion is equivalent to opposite spinal motion.

A patent opening is defined as an unobstructed opening extending through all identified features or structures.

An acute angle is defined as an angle greater than 0 degrees and less than 90 degrees. Two components oriented at an acute relative angle may not be parallel or perpendicular to each other. A compound angle is the resultant angle projected from two angles lying in mutually perpendicular planes.

Foliate is defined as shaped like a leaf. Leaves occur in a multitude of shapes, or two-dimensional profiles. Leaves also have thickness and are therefore three-dimensional structures. Certain leaves are normally creased or puckered so that they have a pronounced three-dimensional shape. The three-dimensional aspect is included in the present definition of foliate.

Sagittate is defined as shaped like an arrowhead. Arrowheads, more properly termed projectile points, occur in a multitude of shapes, or two-dimensional profiles. Projectile points also have thickness and are therefore three-dimensional structures. The three-dimensional attribute is included in the present definition of sagittate. Projectile points also typically comprise a pointed tip, sharpened edges, and a blunt trailing end. At least these attributes are included in the present definition of sagittate.

Figure 1:
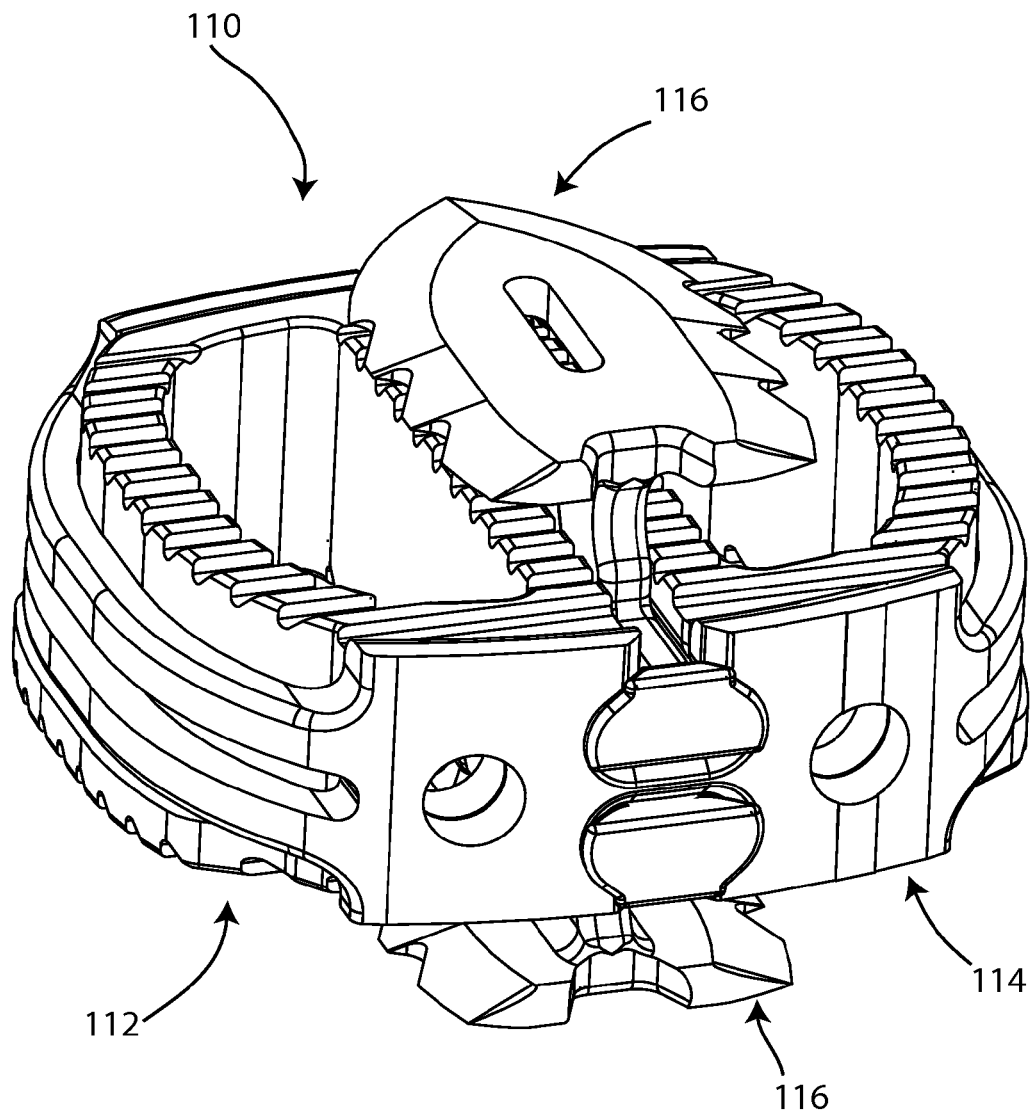
FIG. 1 is a perspective view of the intervertebral fusion prosthesis of FIG. 7, comprising a spacer, a jacket, and two anchors.
Figure 2A:
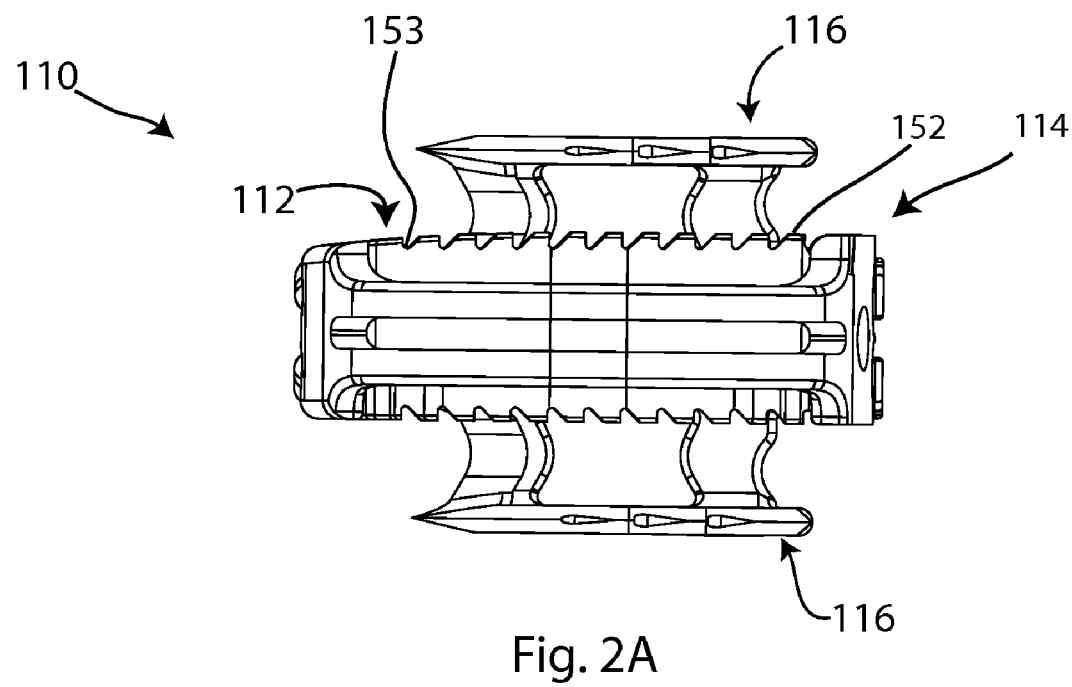
FIG. 2A is a lateral view of the intervertebral fusion prosthesis of FIG. 7.
Figure 2B:
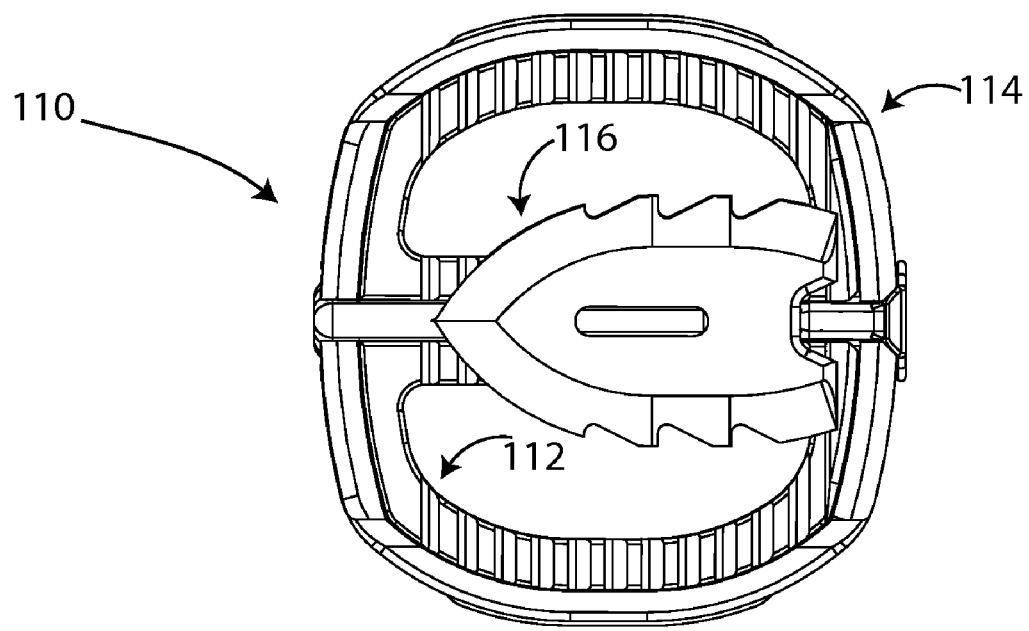
FIG. 2B is a cranial view of the intervertebral fusion prosthesis of FIG. 2A.

Referring to FIGS. 1-2, a prosthesis 110 according to the present invention is shown. The prosthesis 110 comprises an intervertebral spacer 112, a jacket 114, and multiple anchors 116, or bone engagement elements. The present embodiment includes two anchors 116 disposed on opposite sides of the spacer 112. The spacer 112 may fill a portion of an intervertebral disc space between adjacent vertebrae after removal of a portion of an intervertebral disc. The jacket 114 may surround the spacer 112 in approximately the same orientation that an intact annulus fibrosus surrounds a natural intervertebral disc. The anchors 116 may slide into engagement with the spacer 112 and the jacket 114 to rigidly connect the spacer 112 to the vertebral bodies.

Figure 3A:
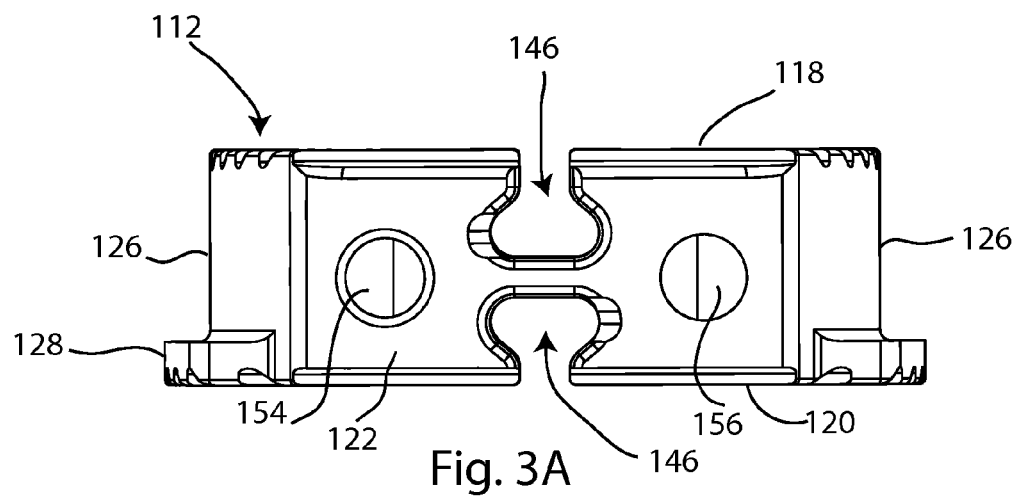
FIG. 3A is an anterior view of the spacer of FIG. 7.
Figure 3B:
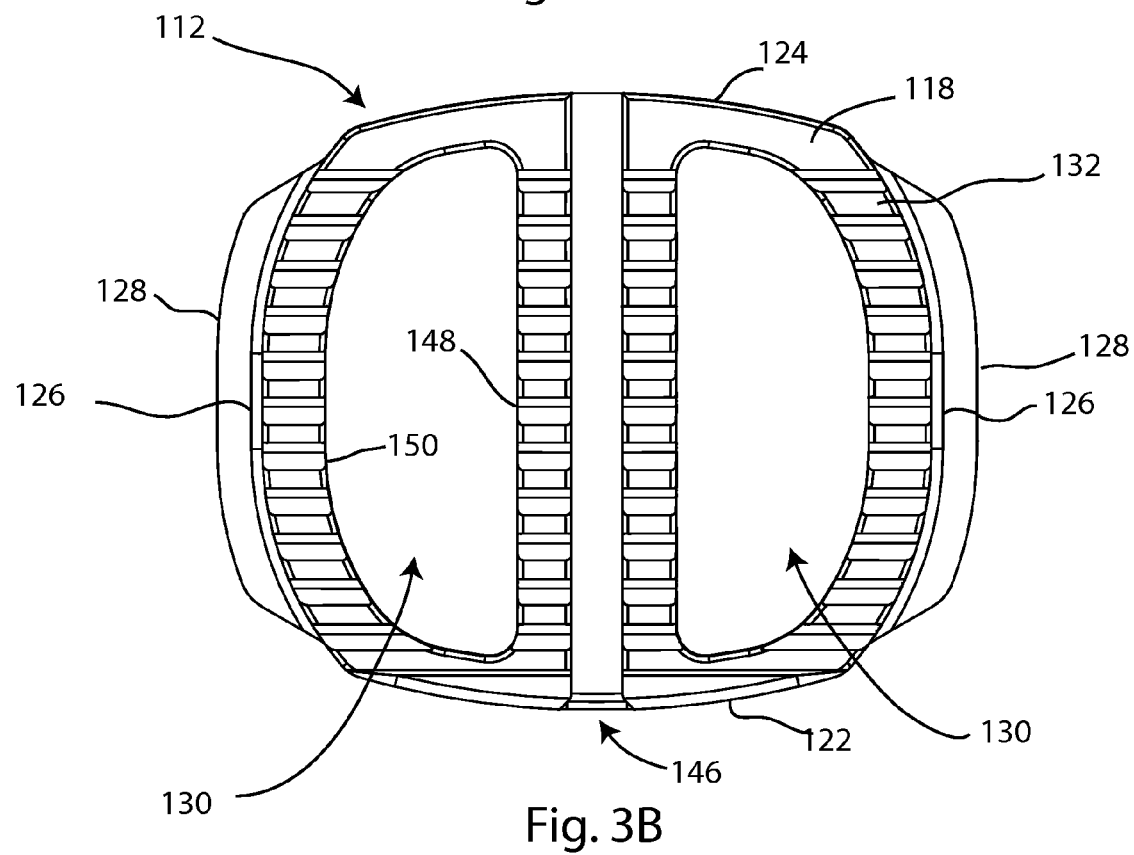
FIG. 3B is a cranial view of the spacer of FIG. 3A.

Referring to FIG. 3, the spacer 112 is illustrated in a front view (FIG. 3A) and a top view (FIG. 3B). The spacer 112 may comprise a top side 118, a bottom side 120 opposite the top side 118, a leading side 124, a trailing side 122 opposite the leading side 124, and two lateral sides 126 extending between the leading 124 and trailing 122 sides. In other words, the spacer 112 may comprise a general three-dimensional body. The present embodiment of the spacer 112 has a generally oval shape in the top view. Alternatively, the spacer 112 may be square, rectangular, circular, elliptical, kidney-shaped, or any other shape in the top view. The top and bottom sides 118, 120 of the spacer 112 may be flat, concave, convex, or any other shape in the front view (FIG. 3A) or lateral view (FIG. 2A). In particular, the top and bottom sides 118, 120 of the spacer 112 may be curved or angled to maintain or restore an anatomically appropriate lordotic or kyphotic angle in the lateral view. In certain embodiments, the various sides of the spacer 112 may blend together to a greater or lesser degree.

The spacer 112 may comprise an interconnection feature extending across the top 118 or bottom side 120. The interconnection feature is shaped and sized to mate with a corresponding interconnection portion of the anchor 116. In the present embodiment, the interconnection feature is a dovetail slot 146 between the leading and trailing sides 124, 122, as shown most clearly in FIG. 5. A first dovetail slot 146 extends across the top side 118 and a second dovetail slot 146 extends across the bottom side 120. Alternatively, the interconnection feature could comprise a T-slot, slide, keyways, ratchets, pins, press-fit components, or threads. The interconnection feature could alternatively comprise a protruding feature corresponding to any of the undercut features previously listed.

The spacer 112 may comprise a ridge 128, or shelf, extending along a lateral side 126 adjacent to the top 118 or bottom side 120. In the embodiment shown, the spacer 112 comprises bilateral ridges 128 adjacent to the bottom side 120. It can be appreciated from FIG. 3 that the ridges 128 increase the surface area of the bottom side 120 relative to the top side 118.

The spacer 112 may optionally have one or more cavities 130 extending through the top and bottom sides 118, 120 to contain bone graft material or to serve as channels for bone growth. Each cavity 130 may extend unobstructed through the spacer 112 so as to comprise a patent opening through the spacer 112. In the present embodiment, the spacer 112 has bilateral cavities 130 separated by a central web 148 and encircled by an annular wall 150. Alternatively, the spacer may have no cavity 130.

The spacer 112 may have one or more instrument connection features on the trailing side 122. In the present embodiment, the spacer 112 has a first hole 154 and a second hole 156 through the wall 150 on the trailing side 122. One or both of the holes 154, 156 may be threaded or provided with other connection means, such as a bayonet socket, notches, or undercuts. In the present embodiment, the first hole 154 is threaded. Alternatively, the instrument connection feature may be a protruding feature such as a post or tab. It is contemplated that the spacer may lack an instrument connection feature altogether.

The top and bottom sides 118, 120 of the spacer 112 may be roughened to prevent in-vivo migration. Alternately, the top and bottom sides 118, 120 of the spacer 112 may be provided with an alternating pattern of ridges 152 and grooves 153, teeth, or other structured surface enhancements. FIG. 2A shows ridges 152 and grooves 153 from a lateral view.

The spacer 112 may comprise radiolucent polyetheretherketone (PEEK) or polyaryletherketone (PAEK). Alternatively, the spacer 112 may comprise a material that is only partially radiolucent, so that the spacer 112 may be visualized radiographically without obscuring a view of any developing intervertebral bone fusion mass. Alternatively, the structure of the spacer 112 may be manipulated to produce partial radiolucence, such as by forming a radiopaque material with grooves, controlled porosity, or other means. In an alternate embodiment, the spacer 112 may comprise autograft bone, allograft bone, or bone graft substitute. The spacer 112 may alternatively comprise metal, ceramic, glass, polymer, or any other material known for use in the human body. The spacer 112 may also comprise one or more surface treatments to encourage bony attachment, such as porous coating, plasma spray coating, hydroxyapatite, or tricalcium phosphate.

Figure 4A:
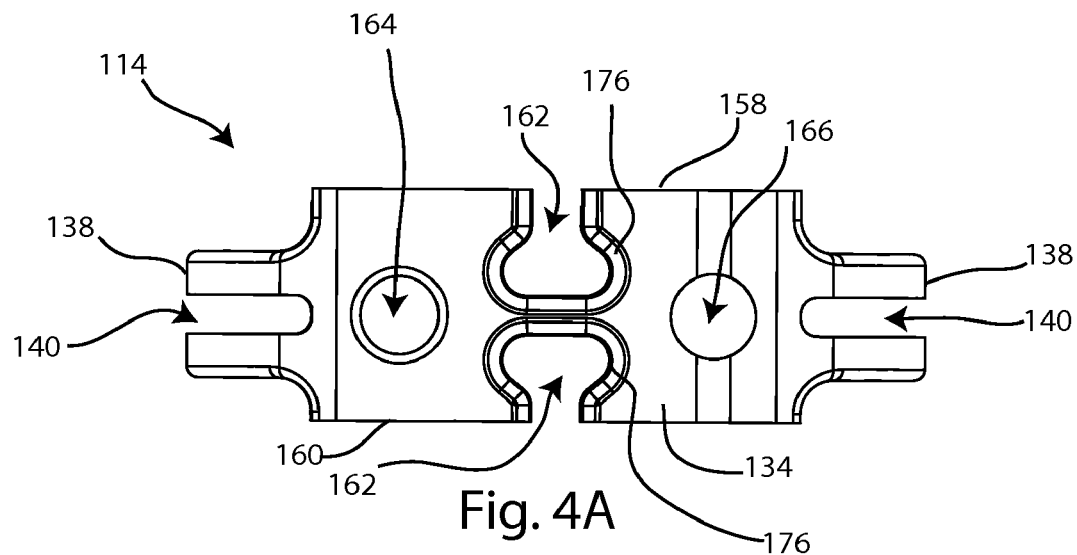
FIG. 4A is an anterior view of the jacket of FIG. 7.
Figure 4B:
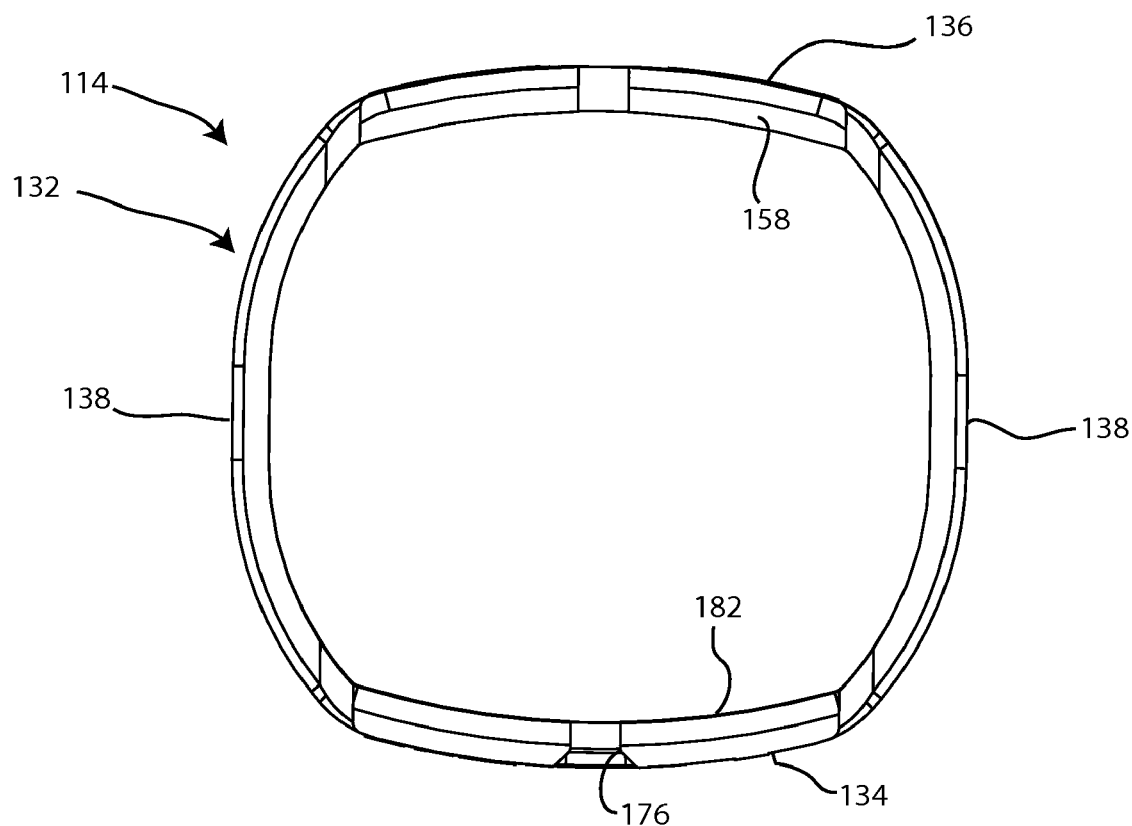
FIG. 4B is a cranial view of the jacket of FIG. 4A.

Referring to FIG. 4, the jacket 114 is illustrated in a front view (FIG. 4A) and a top view (FIG. 4B). The jacket 114 comprises an annular wall 132 extending between a top side 158 and a bottom side 160 and comprising a leading portion 136, a trailing portion 134 opposite the leading portion 136, and two side portions 138 extending between the leading 136 and trailing 134 portions. With reference to FIGS. 1-2, it can be appreciated that the leading 136 and trailing 134 portions of the jacket 114 may extend proximate the top and bottom sides 118, 120 of the spacer 112 when the spacer 112 and jacket 114 are assembled together. However, the side portions 138 may be spaced apart from the top and bottom sides 118, 120. This arrangement may afford an unobstructed post-operative lateral view of any developing bone fusion mass proximate the top and bottom sides 118, 120 of the spacer 112. The present embodiment of the jacket 114 has a generally oval shape in the top view, corresponding closely to the shape of the spacer 112 in the top view. It is contemplated that alternatively shaped jackets may be constructed to correspond closely to the alternative spacer shapes described previously. It is further contemplated that the jacket 114 may be shaped to correspond closely to selected portions of the spacer 112, with a gap being present around the remaining interface. This approach may simplify fabrication of the spacer 112 and the jacket 114 by permit larger manufacturing tolerances, at least in the regions where a gap exists between the spacer 112 and the jacket 114.

The jacket 114 may comprise an interconnection feature extending across the top 156 or bottom side 158. Preferably, the interconnection feature is identical to the interconnection feature of the spacer 112. In the present embodiment, the interconnection feature is a dovetail slot 162 between the leading and trailing portions 136, 134, as shown most clearly in FIG. 5. A first dovetail slot 162 extends across the top side 156 and a second dovetail slot 162 extends across the bottom side 158. The interconnection feature on the jacket 114 may comprise any of the alternative configurations set forth previously with regard to the interconnection feature on the spacer 112.

The jacket 114 may have a window 140 through the side portions 138 through which a developing bone fusion mass may be radiographically observed post-operatively. The window 140 may extend unobstructed through the jacket 114 so as to comprise a patent opening across the jacket 114.

The jacket 114 may have one or more instrument connection features on the trailing portion 134. In the present embodiment, the jacket 114 has a first hole 164 and a second hole 166 through the wall 132 on the trailing portion 134. One or both of the holes 164, 166 may be threaded. In the present embodiment, the first hole 164 is threaded. The jacket may comprise alternative instrument connection features, or no instrument connection feature, as described previously for the spacer 112.

The jacket 114 may be made of metal, ceramic, glass, polymer, or any other structural material known for use in the human body. The jacket 114 may also comprise one or more surface treatments to encourage bony attachment, such as porous coating, plasma spray coating, hydroxyapatite, or tricalcium phosphate. In an alternate embodiment, the jacket 114 may comprise autograft bone, allograft bone, or bone graft substitute.

Figure 5:
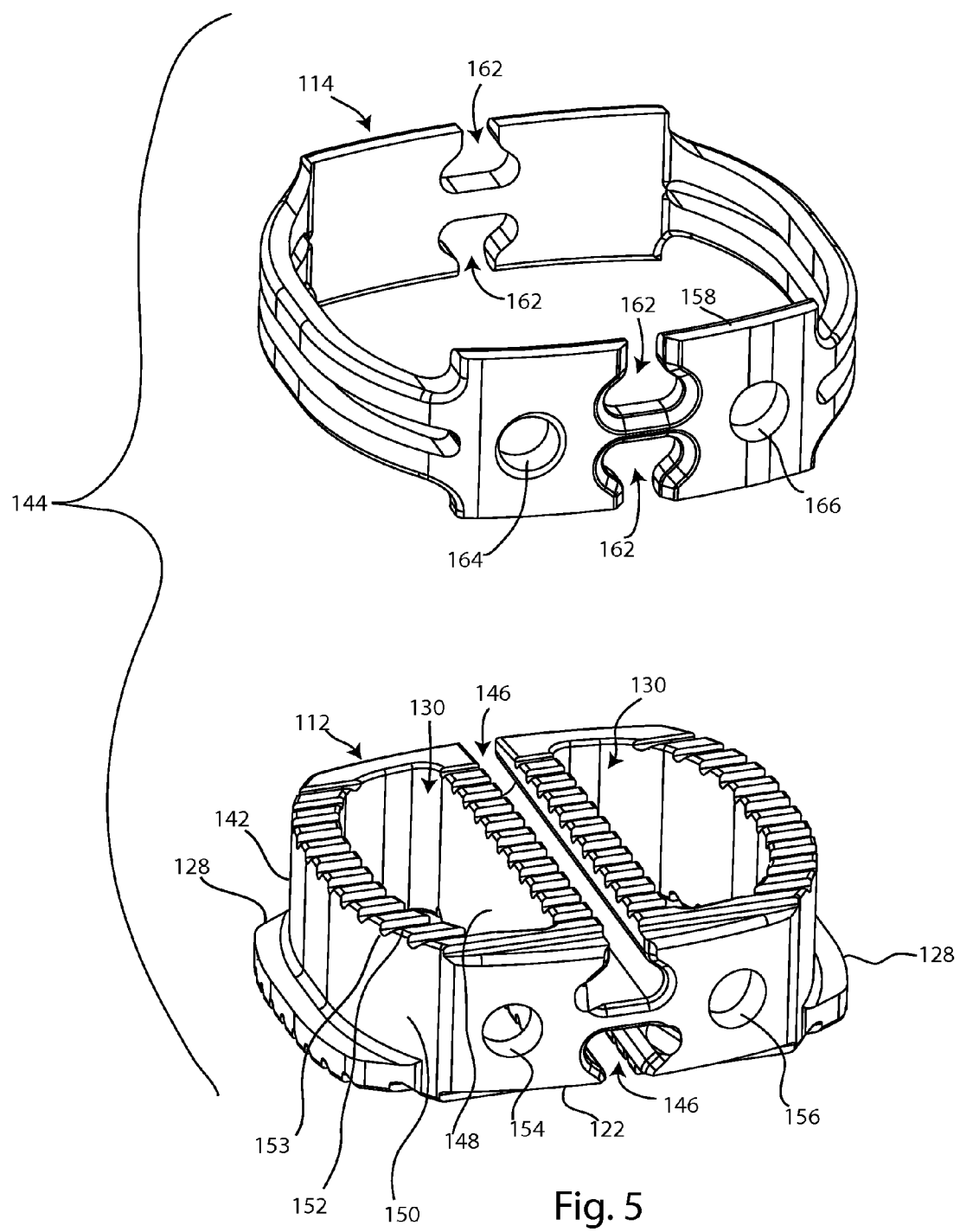
FIG. 5 is an exploded perspective view of the spacer and jacket of FIG. 7.

Referring to FIG. 5, an exploded perspective view illustrates the jacket 114 and the pacer 112. The jacket 114 may fit snugly over an outer perimeter surface 142 of the spacer 112 so that the spacer 112 and jacket 114 form a spacer assembly 144. Referring to FIGS. 3-5, when the spacer 112 and the jacket 114 are assembled, the leading portion 136 of the jacket 114 is adjacent to the leading side 124 of the spacer 112, the trailing portion 134 of the jacket 114 is adjacent to the trailing side 122 of the spacer 112, the side portions 138 of the jacket 114 are adjacent to the lateral sides 126 of the spacer 112, the top side 158 of the jacket 114 is proximate the top side 118 of the spacer 112, and the bottom side 160 of the jacket 114 is proximate the bottom side 120 of the spacer 112. In this case, the ridge 128 on the spacer 112 may abut a side portion 138 of the jacket 114 when the spacer 112 and jacket 114 are assembled.

With reference to FIGS. 3-5, the spacer assembly 144 may have an interconnection feature that extends across the spacer 112 and the jacket 114. In the present embodiment, the spacer assembly 144 comprises two interconnection features, one extending across the top side 118 of the spacer 112 and one extending across the bottom side 120 of the spacer 112. Each interconnection feature comprises the dovetail slot 146 of the spacer 112 which aligns with the dovetail slot 162 in the jacket 114 so as to form a single continuous interconnection feature across the spacer assembly 144, as is most clearly seen in FIG. 1. The dovetail slot 146, 162 captures the interconnection portion of the anchor 116 and transmits tension, compression, shear, torsion, and bending loads between the anchor 116 and the spacer. In the present embodiment, spinal loads are distributed from one vertebra to another through the anchors 116 and across the leading and trailing portions 136, 134 of the jacket 114. When this embodiment is implanted from an anterior approach, the leading portion 136 of the jacket 114 is in the posterior portion of the intervertebral space and the trailing portion 134 of the jacket 114 is in the anterior portion of the intervertebral disc space. With this arrangement, the prosthesis 110 may replicate the strength and stiffness of the natural anterior and posterior longitudinal ligaments to provide superior fixation of adjacent vertebral bodies.

Figure 6A:
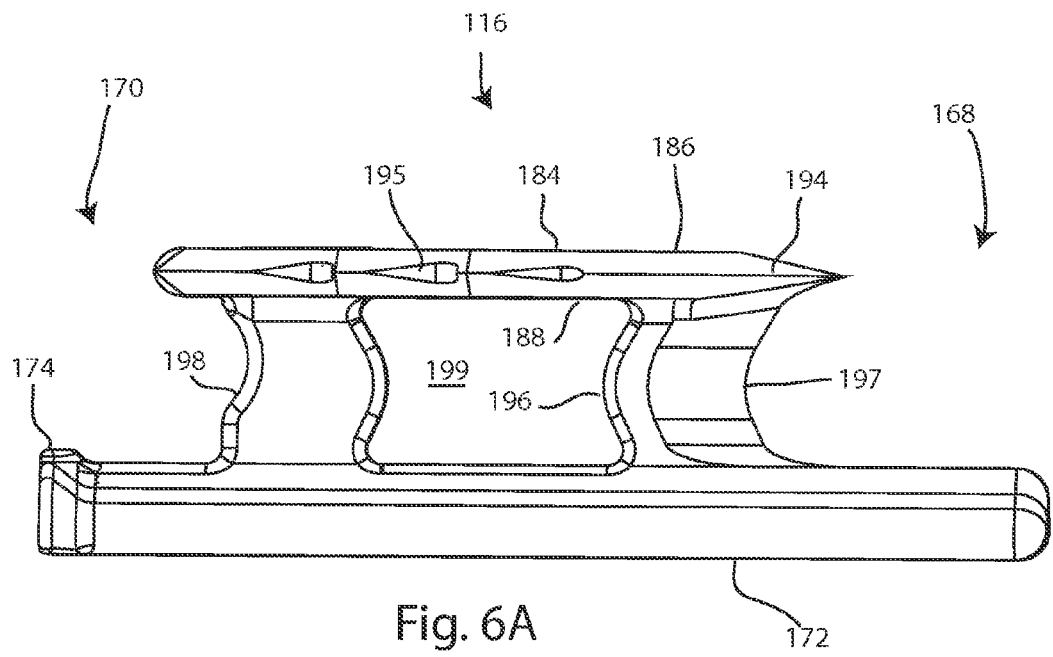
FIG. 6A is a lateral view of the anchor of FIG. 7.
Figure 6B:
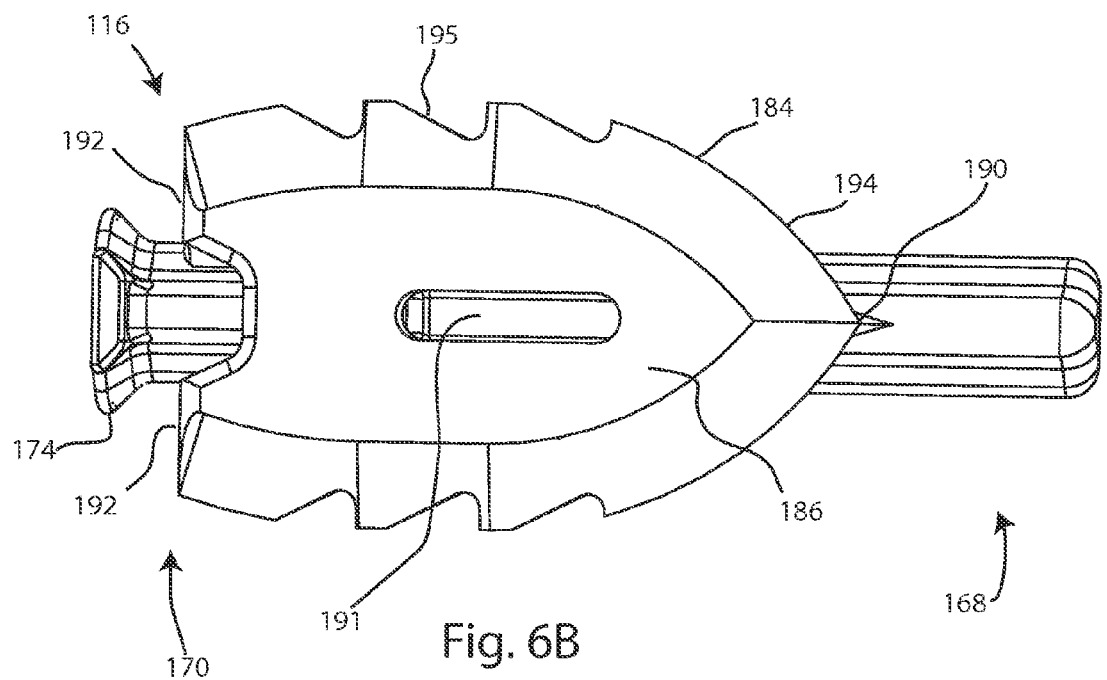
FIG. 6B is a cranial (or caudal) view of the anchor of FIG. 6A.

Referring to FIG. 6, the anchor 116 is illustrated in a side view (FIG. 6A) and a top view (FIG. 6B). The anchor 116 may be generally elongate with a leading end 168 and a trailing end 170 opposite the leading end 168. Anchors of different sizes and shapes may be provided.

The anchor 116 may comprise an interconnection portion extending between the leading and trailing ends 168, 170. The interconnection portion may be shaped and sized to mate with the interconnection feature previously described for the spacer assembly 144, so as to slidably connect the anchor 116 to the spacer assembly 144. In the present embodiment, the interconnection portion of the anchor 116 is a dovetail beam 172. When the anchor 116 is fully engaged with the spacer assembly 144, the dovetail beam 172 engages the leading portion 136 and trailing portion 134 of the jacket 114 so that load may be transmitted between the anchor 116 and the jacket 114 across opposite sides of the jacket 114. The interconnection portion may alternatively comprise a T-rail, slide, key, ratchets, pins, press-fit components, or threads. The interconnection feature could alternatively comprise an undercut feature corresponding to any of the protruding features previously listed.

The anchor 116 may comprise a stop feature that prevents the anchor 116 from advancing too far into the spacer assembly 144 at the time of implantation, or migrating toward the leading portion 136 of the jacket 114 post-operatively. In the present embodiment, the stop feature is a flange 174, or enlarged tip, integrated on the dovetail beam 172 at the trailing end 170. The outer profile of the flange 174 is larger than the profile of the mating dovetail slot 162 in the jacket 114. Therefore, the flange 174 cannot pass into the dovetail slot 162. The flange 174 may taper or flare from the dovetail beam 172 toward the trailing end 170. A matching chamfer 176 may be present around the dovetail slot 162, so that the flange 174 may be at least partially recessed within the trailing portion 134 of the jacket wall 132. The congruent tapered surfaces of the flange 174 and the chamfer 176 provide a more uniform stress distribution than may be present with point-to-point or point-to-surface contact. This maximizes the load bearing capability of the flange 174 and chamfer 176.

Figure 9:
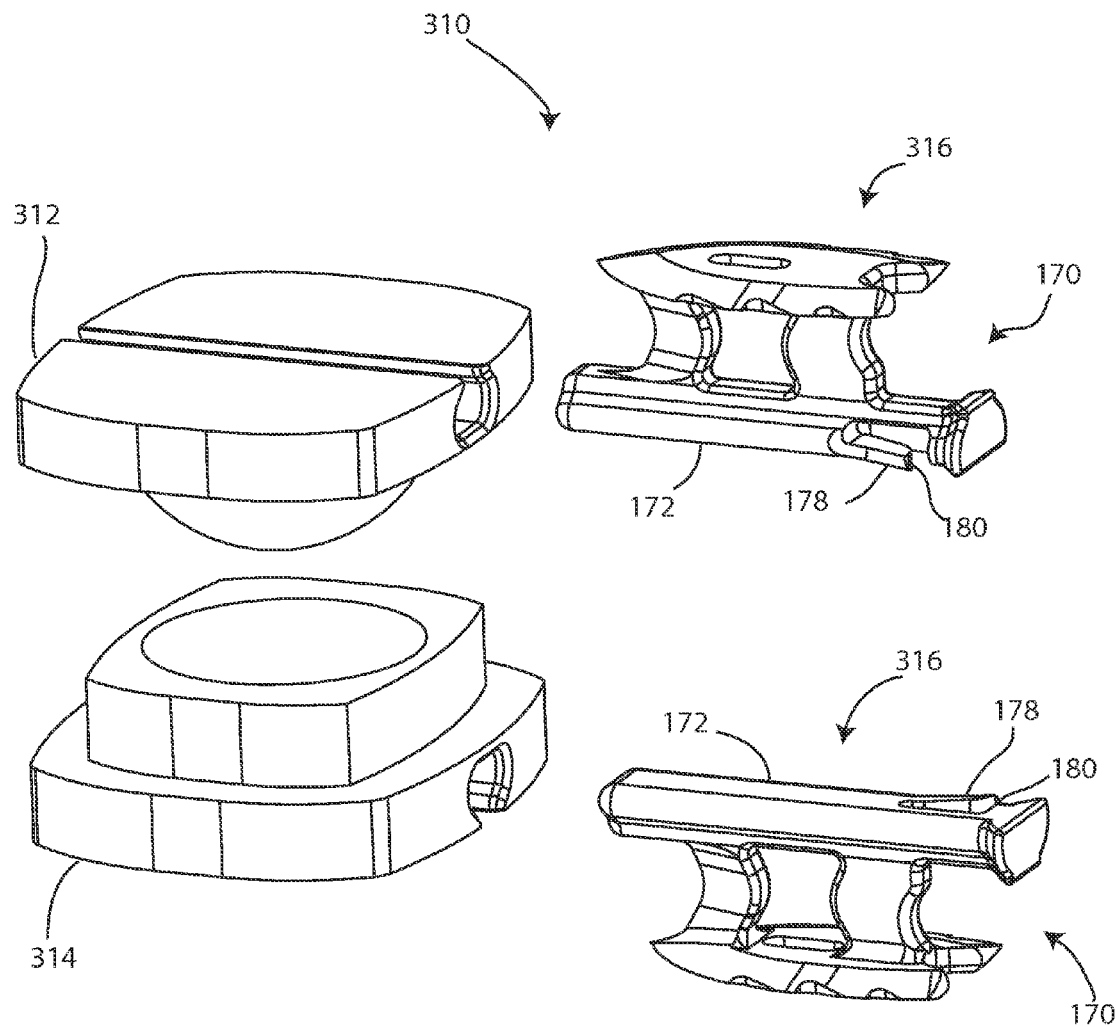
FIG. 9 is an exploded perspective view of a motion-preserving total disc replacement prosthesis.

The anchor 116 may comprise a locking feature that prevents the anchor from migrating toward the trailing portion 134 of the jacket 114 post-operatively. In the present embodiment, the locking feature is a flexible tab 178 integrated on the dovetail beam 172 proximate the trailing end 170, as best seen in FIG. 9. As the dovetail beam 172 advances into the spacer assembly 144, the tab 178 contacts the trailing portion 134 of the jacket 114 and elastically deforms toward the dovetail beam 172. As the dovetail beam 172 advances further into the spacer assembly 144, the tab 178 slides past the trailing portion 134 of the jacket 114 and springs away from the dovetail beam 172 so that the tip 180 of the tab 178 makes surface-to-surface contact with an inner surface 182 of the jacket 114. Thus, the tab 178 prevents the anchor 116 from migrating toward the trailing portion 134 of the jacket 114 post-operatively. The locking feature may alternatively snap into engagement with the trailing side 122 of the spacer 112. The locking feature may alternatively be integrated into the jacket 114 or into the spacer 112.

The anchor 116 may comprise a fixation portion that rigidly secures the anchor 116 to a bone. More specifically, the fixation portion may resist axial tensile and compressive forces resulting from, for example, spinal flexion and extension or right and left lateral bending. The fixation portion may extend between the leading and trailing ends 168, 170 of the anchor, and may be spaced apart from the interconnection portion described previously. In the present embodiment, the fixation portion is a plate 184 extending between the leading and trailing ends 168, 170 of the anchor. The plate 184 comprises two broad surfaces, a top side 186 and a bottom side 188 opposite the top side 186. In the present embodiment, the bottom side 188 of the plate 184 is oriented to squarely face the dovetail beam 172.

Referring to FIG. 6B, the present embodiment of the plate 184 has a top view profile that resembles a leaf or an arrowhead. Thus, the plate 184 can be described as foliate (shaped like a leaf) or sagittate (shaped like an arrowhead). The plate 184 tapers to a point 190 at the leading end 168 and terminates in a blunt edge 192 at the trailing end 170. The pointed leading end 168 reduces the magnitude of the force required for insertion and to minimize collateral damage to the vertebral body. An optional window 191 may pierce the plate 184.

The present embodiment of the plate 184 is flat in the side view, as seen in FIG. 6A. Alternatively, plate 184 could be bent, curved, rounded, or otherwise shaped to resemble a "T", "L", "O", "Y", "V", rectangle, circle, oval, concave, convex, and variations thereof in the side view, or alternately, in a view from the leading end 168 or trailing end 170.

Referring to FIG. 6A, with brief reference to FIG. 1, the present embodiment of the plate 184 is sharpened around at least a portion of its profile to produce a cutting edge 194 capable of cutting through bone. More precisely, the cutting edge 194 may extend along lateral sides of the plate to the point 190, while the blunt edge 192 may preferably be left unsharpened to resist migration after insertion. Alternatively, the cutting edge 194 may extend only along the portion of the profile that faces toward the leading end 168. The cutting edge 194 may be V-shaped, convex, hollow ground, or any other cutting edge shape. In a preferred embodiment, the cutting edge 194 may be produced with a curved face adjacent the bottom side 188 and a flat face adjacent the top side 186. In an alternative embodiment, the plate 184 may be sharpened asymmetrically so that the cutting edge 194 is located closer to the top side 186 than to the bottom side 188. By producing the cutting edge 194 with a curved face and a flat face, or by asymmetrically locating the cutting edge 194 proximate to the top side 186, the plate 184 may be biased to track along a path that diverges at least slightly from the path taken by the dovetail beam 172 as the anchor 116 slides into engagement with the spacer assembly 144 and adjacent vertebrae. In other words, this configuration naturally biases the anchor 116 to lift away from the dovetail beam 172 when the plate 184 is inserted into bone. When two or more anchors 116 according to this preferred embodiment are inserted on opposite sides of the spacer assembly 144 to engage adjacent vertebrae, the vertebrae are compressed against the spacer assembly 144 as the anchors 116 are advanced. Additionally, the cutting edge 194 may be interrupted by saw teeth or serrations 195 to resist migration after insertion.

The anchor 116 may comprise a leg 196 extending generally perpendicularly between the interconnection portion and the fixation portion. In the present embodiment, a first leg 196 extends between the dovetail beam 172 and the plate 184. The first leg 196 is disposed toward the leading end 168 of the anchor 116. A second leg 198 extends between the dovetail beam 172 and the plate 184 and is disposed toward the trailing end 170 of the anchor 116. This arrangement provides a window 199, or patent opening, between the legs 196, 198, so that any developing bone fusion mass may be radiographically observed post-operatively. A cutting edge 197 capable of cutting through bone may be present on the first leg 196, on a side proximate the leading end 168 of the anchor 116. Alternatively, the leg may be configured to avoid penetrating bone at all.

The anchor 116 may alternatively comprise any of a variety of features to resist migration after insertion, such as teeth, keels, prongs, fish hooks, or barbs to engage the bone or the spacer 112.

The anchor 116 may be made of metal, ceramic, glass, polymer, or any other structural material known for use in the human body. The anchor 116 may also comprise one or more surface treatments to encourage bony attachment, such as porous coating, plasma spray coating, hydroxyapatite, or tricalcium phosphate. In an alternate embodiment, the anchor 116 may comprise autograft bone, allograft bone, or bone graft substitute.

Figure 7:
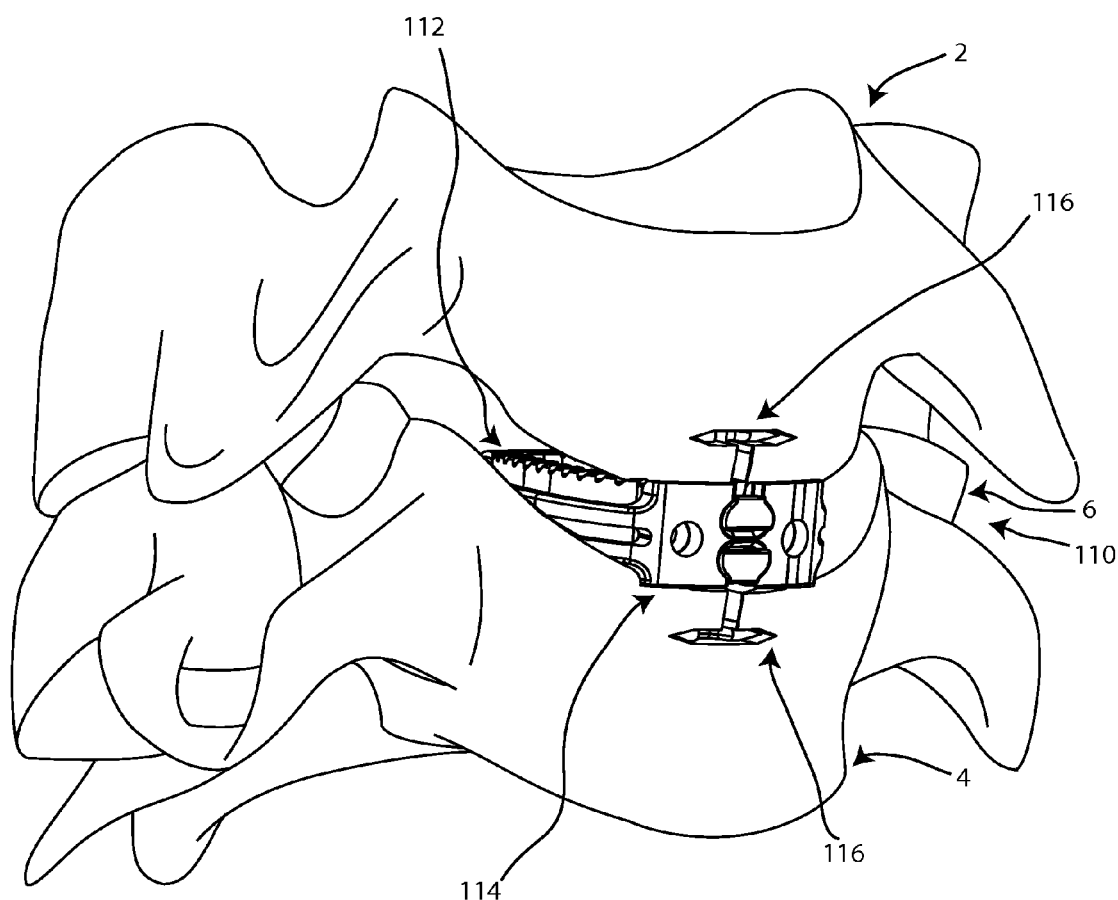
FIG. 7 is a perspective view of an intervertebral fusion prosthesis inserted into an intervertebral space between two adjacent cervical vertebrae.

Referring to FIG. 7, the prosthesis 110 is shown implanted in an intervertebral space 6 between adjacent cervical vertebrae 2, 4. It can be appreciated that the spacer 112 of prosthesis 110 may be sized and shaped to at least partially fill an intervertebral disc space between adjacent vertebrae at any level of the spine after removal of at least a portion of an intervertebral disc.

Methods of implanting the intervertebral fusion prosthesis 110 in the cervical spine from an anterior surgical approach will now be described with reference to FIG. 7. It is understood that the same or similar methods may be employed to implant the prosthesis 110 at any level of the spine, and from any surgical approach, without departing from the scope of the present invention. More specifically, it is contemplated that prosthesis 110 may be implanted from an anterior, posterior, lateral, transforaminal, or other surgical approach.

At least a portion of an intervertebral disc 8 (not shown) between adjacent cervical vertebrae 2, 4 may be removed from the intervertebral disc space 6, using tools and techniques known in the art. Substantially all of the disc 8 may be removed in the present embodiment.

The spacer assembly 144 having a size and shape corresponding to the disc space 6 may be selected from a kit comprising spacer assemblies of various sizes and shapes. The spacer assembly 144 may be oriented so that the top side 118 of the spacer 112 faces superiorly and the bottom side 120 of the spacer 112 faces inferiorly. The spacer assembly 144 may be further oriented so that the leading side 124 of the spacer 112 faces posteriorly and the trailing side 122 of the spacer 112 faces anteriorly. The spacer assembly 144 is inserted into the disc space 6 between vertebrae 2, 4 from anterior to posterior until the spacer assembly 144 is generally concentric with the adjacent vertebral bodies of vertebrae 2, 4.

A first anchor 116 having a size and shape corresponding to the disc space 6 and vertebral bodies of vertebrae 2, 4 may be selected from a kit comprising anchors of various sizes and shapes. The anchor 116 may be oriented so that the plate 184 faces superiorly and the dovetail beam 172 faces inferiorly. The anchor 116 may be further oriented so that the leading end 168 faces posteriorly, the trailing end 170 faces anteriorly, and the dovetail beam 172 is collinear with the dovetail slot 162 across the top side 158 of the jacket 114 and the dovetail slot 146 across the top side 118 of the spacer 112. The dovetail beam 172 of the anchor 116 is inserted into the dovetail slots 162, 146 from anterior to posterior until the dovetail beam 172 engages the leading portion 136 and trailing portion 134 of the jacket 114, the flange 174 abuts the chamfer 176, and the tab 178 snaps behind the inner surface 182 of the jacket 114.

A second anchor 116 may be selected from the kit and oriented so that the plate 184 faces inferiorly, the dovetail beam 172 faces superiorly, the leading end 168 faces posteriorly, the trailing end 170 faces anteriorly, and the dovetail beam 172 is collinear with the dovetail slots 162, 146 across the bottom sides 160, 120 of the jacket 114 and spacer 112. The dovetail beam 172 of the anchor 116 is inserted as described previously.

In a preferred embodiment, the spacer assembly 144 is placed in the intervertebral space 6 first, followed by anchors 116 which secure the spacer assembly 144 to the vertebral bodies of adjacent vertebrae 2, 4. Alternatively, the spacer assembly 144 and anchors 116 may be pre-assembled and subsequently inserted into the disc space 6 as a unit, or the anchors 116 may be inserted into the vertebral bodies of vertebrae 2, 4, followed by the spacer assembly 144.

Referring to FIG. 7, the prosthesis 110 may provide a stable construct by ensuring both anterior and posterior rigid fixation of the adjacent vertebral bodies of vertebrae 2, 4, when implanted from an anterior approach. In general, the more rigid the fixation, the more conducive the environment is to bony fusion. Traditional spinal fusion procedures form stable constructs by relying upon a spacer that is used in combination with a plate or a rod and screw system. The current embodiment may provide the same stability as a traditional spinal fusion construct, but with reduced surgical time as well as the potential for reduced complications associated with secondary hardware outside of the intervertebral space. Newer products on the market only provide anterior tensile load paths, through the use of bone screws or keels. The present embodiment of prosthesis 110 utilizes sliding anchors 116 that connect the anterior and posterior ends of the spacer assembly 144 to the adjacent vertebral endplates. This non-screw based approach leads to a more symmetric stiffness profile of the construct, as well as a reduced radiographic profile. Additionally, the prosthesis 110 may be implanted without using instruments at extreme oblique angles, which reduces complexity for the surgeon.

Figure 8:
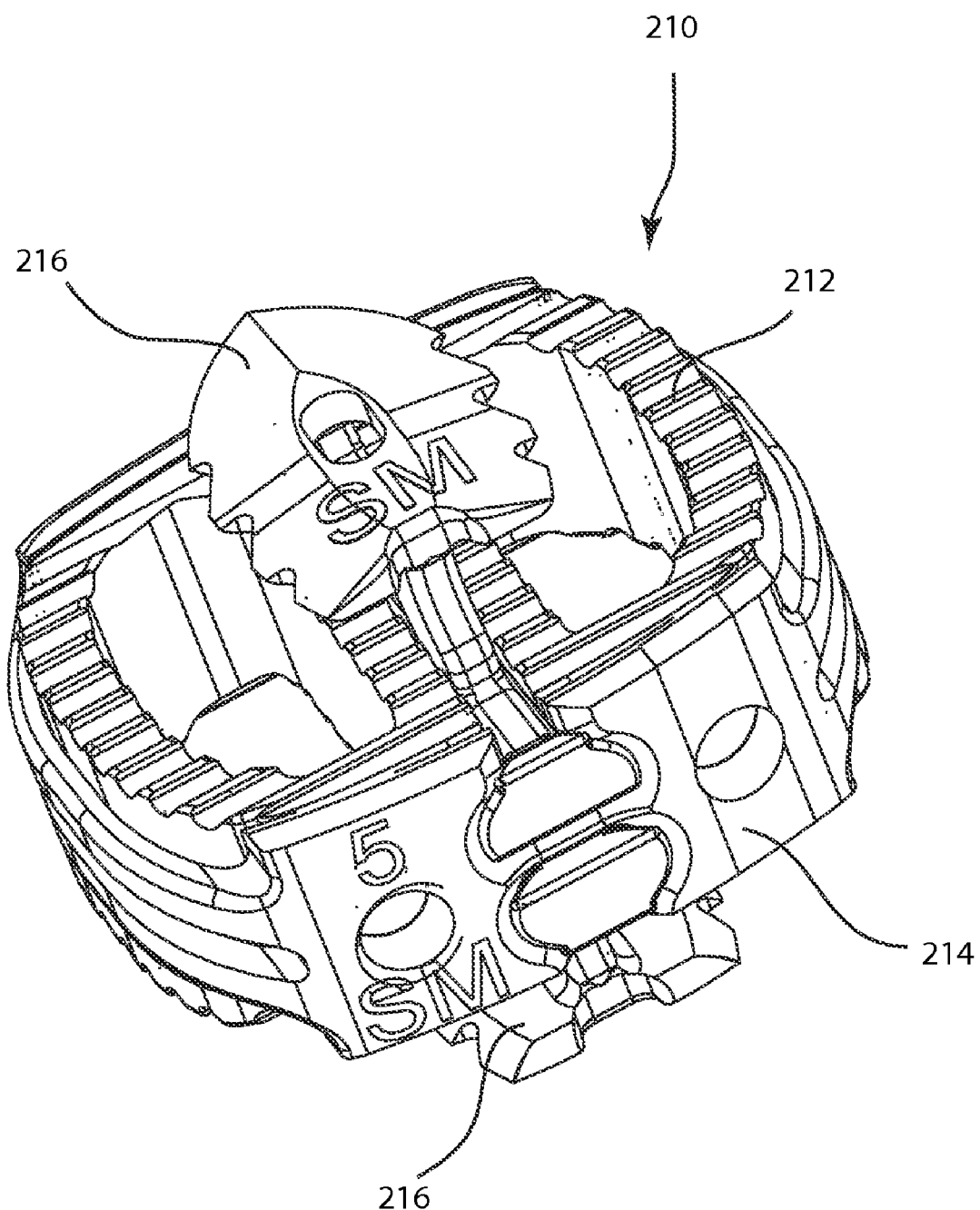
FIG. 8 is a perspective view of an alternate embodiment of an intervertebral fusion prosthesis comprising a spacer, a jacket, and two anchors.

Referring to FIG. 8, an alternate embodiment of an intervertebral fusion prosthesis 210 is shown. The prosthesis 210 comprises an intervertebral spacer 212, a jacket 214, and two anchors 216 disposed on opposite sides of the spacer 212. The anchors 216 slidingly engage the jacket 214 and spacer 212 in the manner described previously.

Referring to FIG. 9, a motion-preserving total disc replacement prosthesis 310 is illustrated in an exploded perspective view. The prosthesis 310 comprises a convex articular component 312, a concave articular component 314 shaped to articulate with the convex articular component 312, and two anchors 316 disposed on opposite sides of the prosthesis 310. The anchors 316 slidingly engage the convex articular component 312 and concave articular component 314 in the manner described previously. In the present embodiment, the anchors 316 provide primary fixation of the prosthesis 310 to adjacent vertebrae. The articular components 312, 314 may each comprise an articular surface integrally formed with an endplate, or alternatively, the articular components may each comprise an articular surface secured to a separate endplate.

Figure 10:
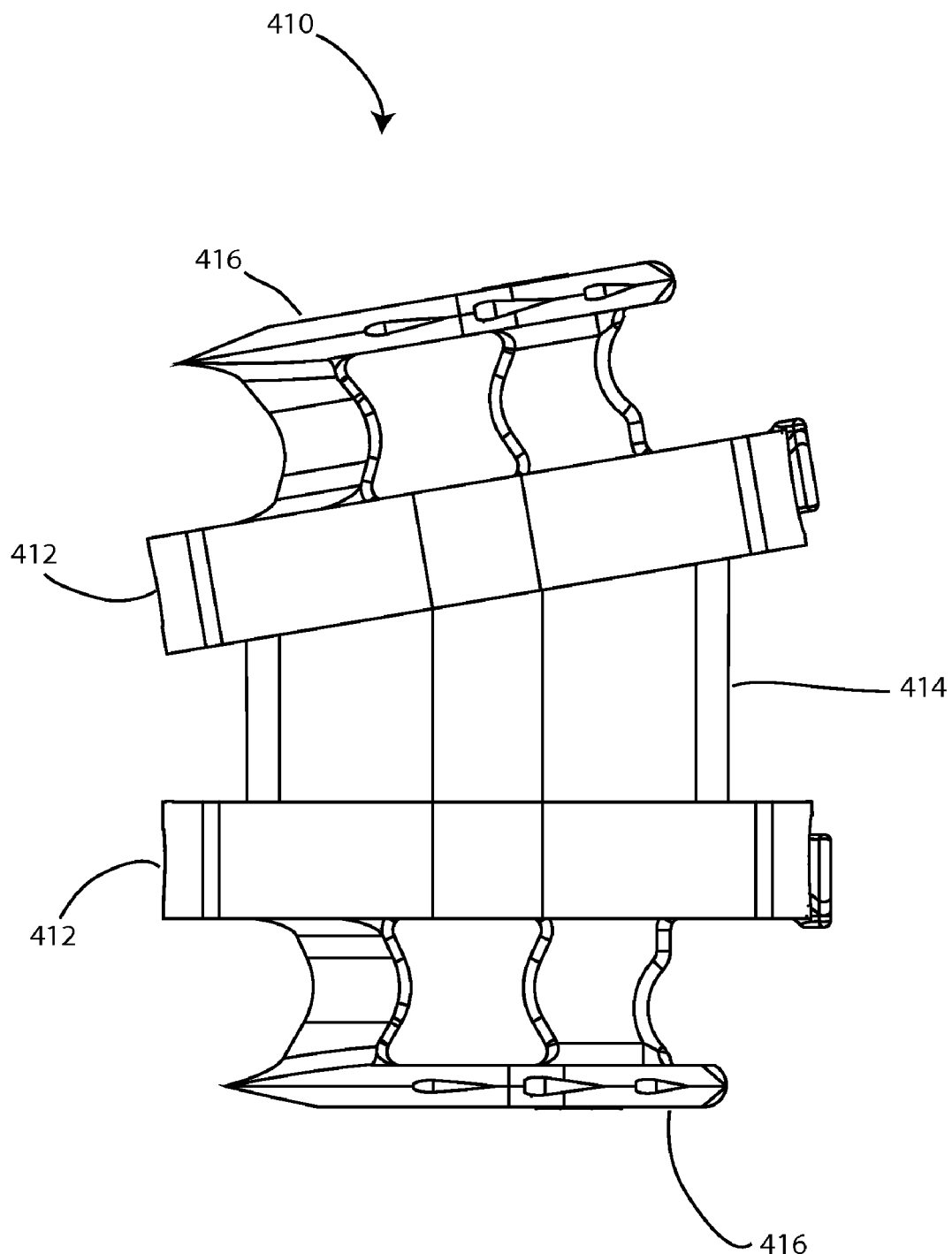
FIG. 10 is a lateral view of an alternate embodiment of a motion-preserving total disc replacement prosthesis.

Referring to FIG. 10, an alternate embodiment of a motion-preserving total disc replacement prosthesis 410 is illustrated in a lateral view. The prosthesis 410 comprises two endplates 412, an elastomeric disc component 414 disposed between the endplates 412, and two anchors 416 disposed on opposite sides of the prosthesis 410. The anchors 416 slidingly engage the endplates 412 in the manner described previously.

Figure 11:
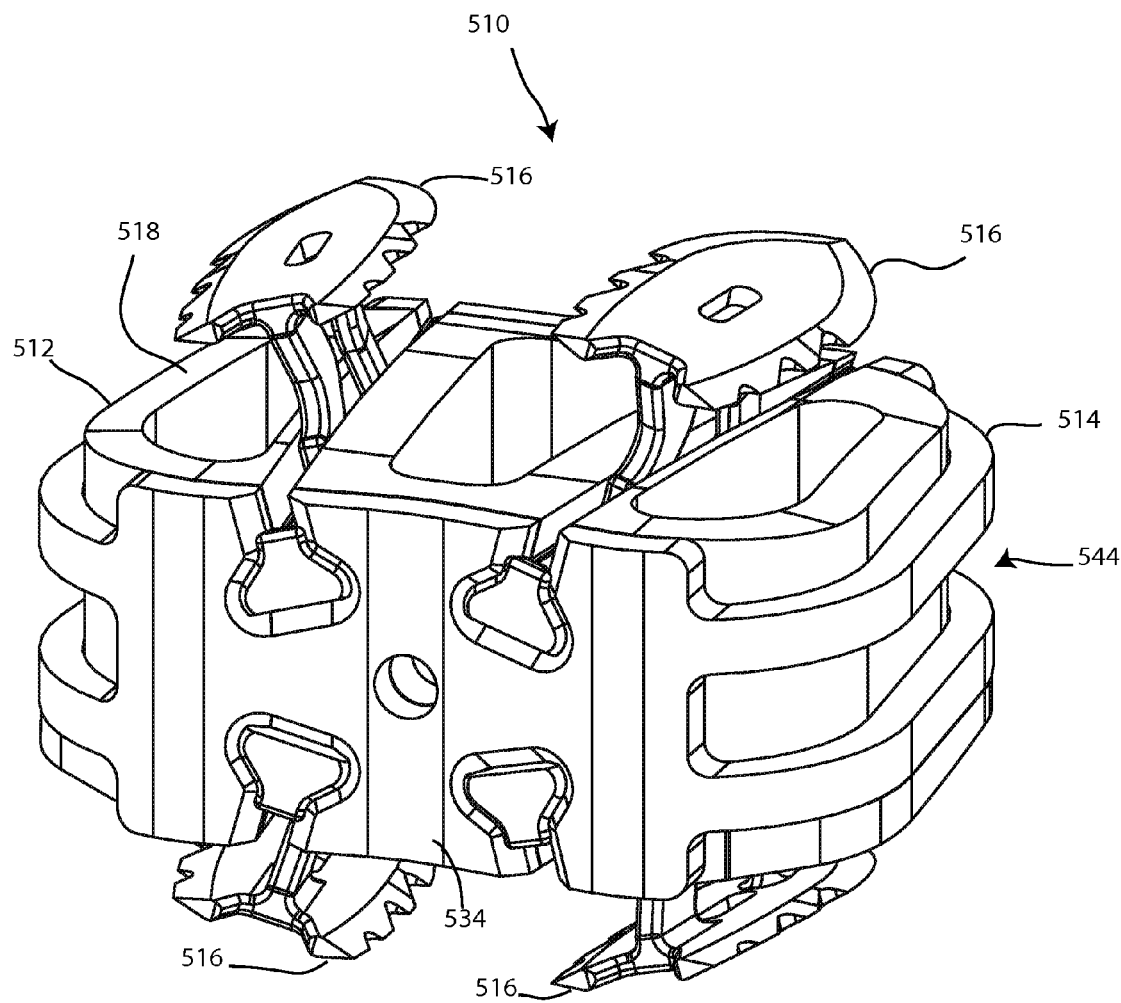
FIG. 11 is a perspective view of an alternate embodiment of an intervertebral fusion prosthesis, comprising a spacer, a jacket, and four anchors.
Figure 12:
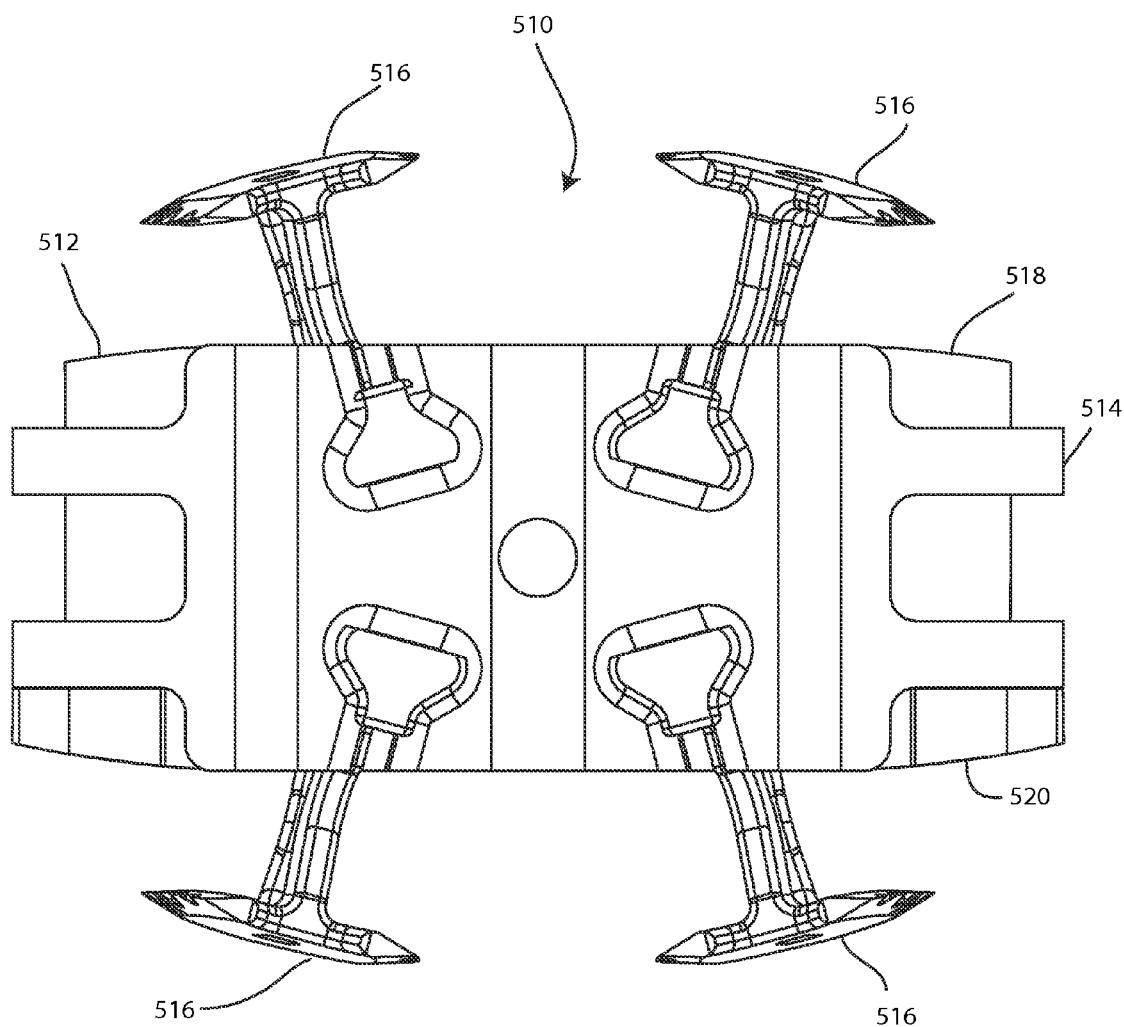
FIG. 12 is an anterior view of the intervertebral fusion prosthesis of FIG. 11.
Figure 13:
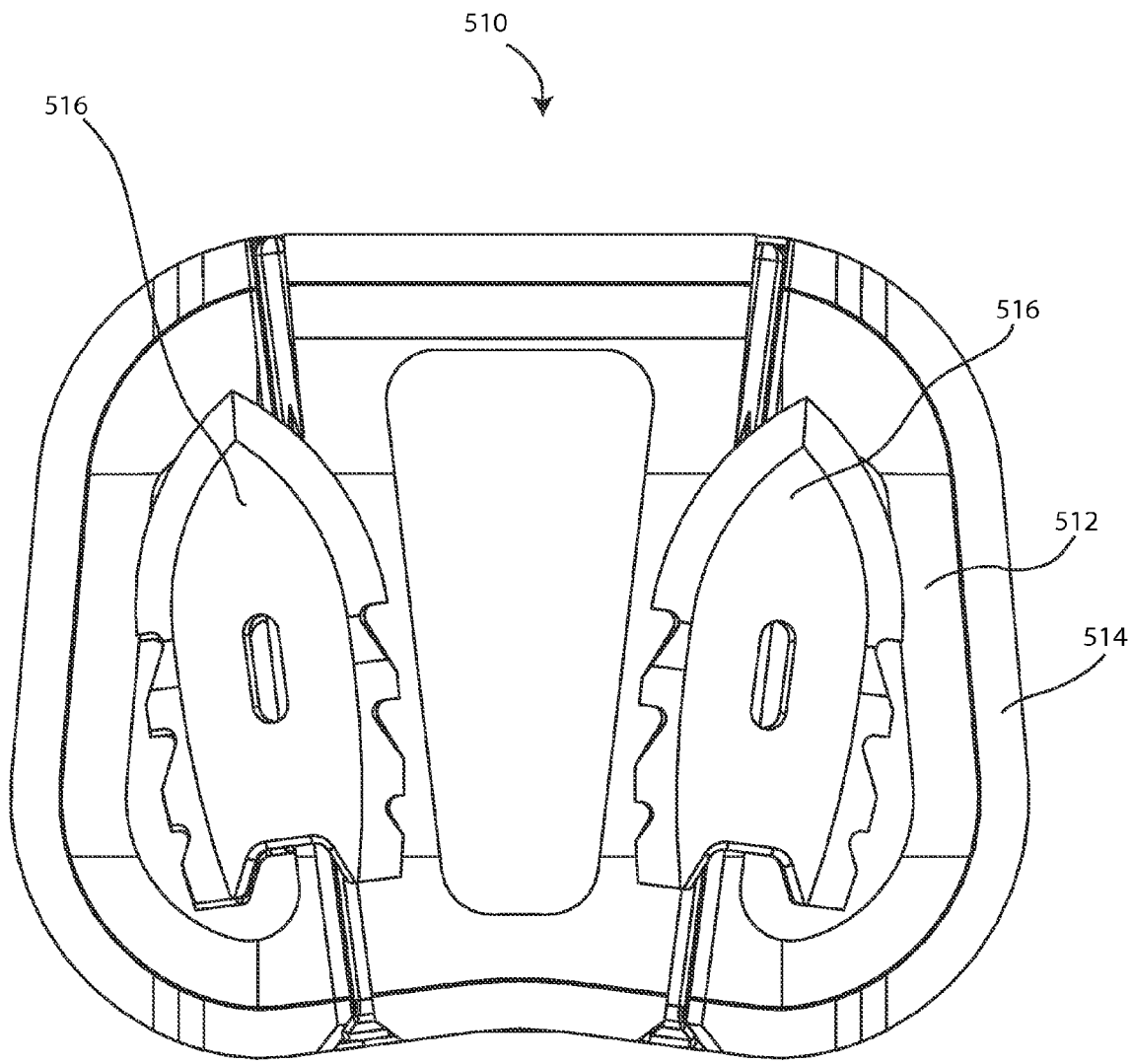
FIG. 13 is a cranial view of the intervertebral fusion prosthesis of FIG. 11.

Referring to FIGS. 11-13, an alternate embodiment of an intervertebral fusion prosthesis 510 is illustrated. Prosthesis 510 comprises a spacer 512, a jacket 514, and four anchors 516.

Figure 14:
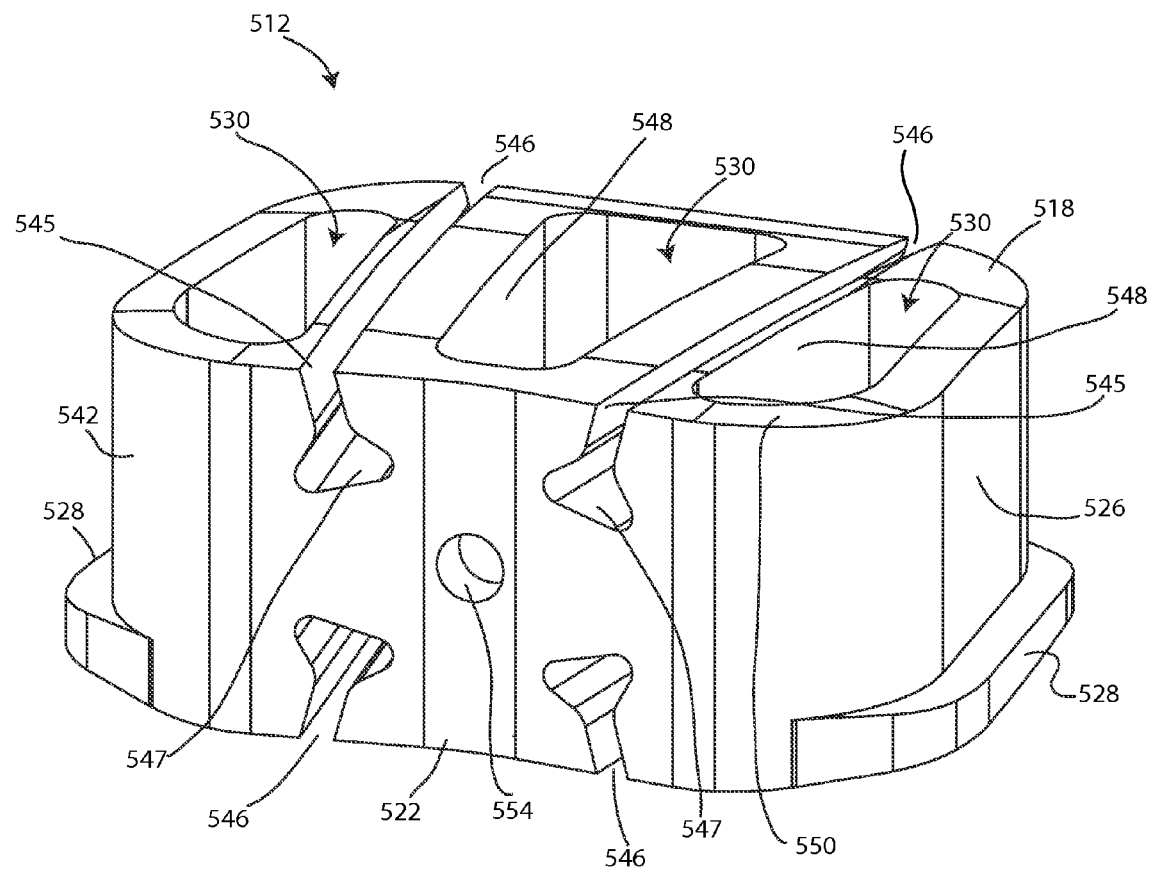
FIG. 14 is a perspective view of the spacer of FIG. 11.
Figure 15A:
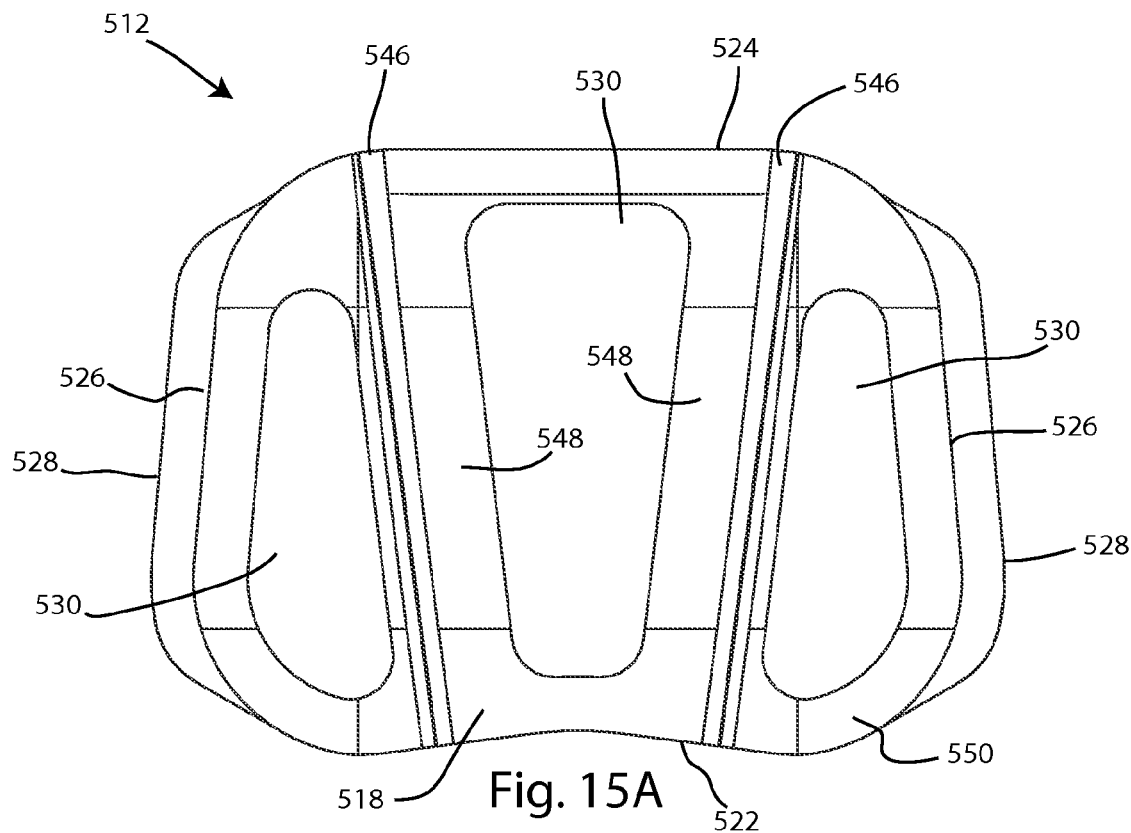
FIG. 15A is a cranial view of the spacer of FIG. 11.
Figure 15B:
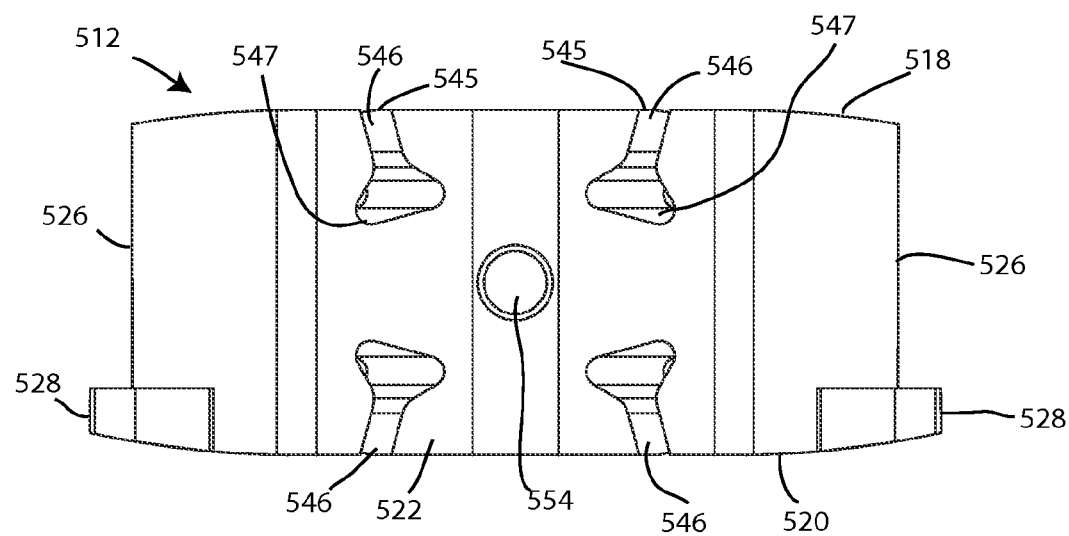
FIG. 15B is an anterior view of the spacer of FIG. 15A.

Referring to FIGS. 14-15, the spacer 512 is illustrated in a perspective view (FIG. 14), a top view (FIG. 15A) and a front view (FIG. 15B). The spacer 512 comprises a top side 518, a bottom side 520 opposite the top side 518, a leading side 524, a trailing side 522 opposite the leading side 524, and two lateral sides 526 extending between the leading 524 and trailing 522 sides. The spacer 512 has a generally kidney-shaped profile in the top view. The top and bottom sides 518, 520 of the spacer 512 are gently contoured in the front view.

In the present embodiment, the spacer 512 comprises four dovetail slots 546 between the leading and trailing sides 524, 522, as shown most clearly in FIG. 14. Two dovetail slots 546 extend across the top side 518 and two dovetail slots 546 extend across the bottom side 520. With reference to FIG. 15A, the dovetail slots 546 on the top side 518 are disposed at an acute angle relative to each other in a first plane parallel to the top side 518, such as the top view plane. The dovetail slots 546 are farther apart at the leading side 524 and closer together at the trailing side 522. With reference to FIG. 15B, the dovetail slots 546 on the top side 518 are also disposed at an acute angle relative to each other in a second plane perpendicular to the first plane, such as the front view plane. An open end 545 of each dovetail slot 546 is farther apart at the top side 518 and a closed end 547 of each dovetail slot 546 is closer together deep within the spacer 512. It can also be appreciated that the closed ends 547 of the dovetail slots are mutually tilted at an acute angle. Thus, the dovetail slots 546 on the top side 518 may be said to be oriented at a compound acute relative angle. The dovetail slots 546 on the bottom side 520 are similarly oriented in this embodiment.

The spacer 512 comprises a ridge 528, or shelf, extending along a lateral side 526 adjacent to the bottom side 520.

The spacer 512 has three cavities 530 extending through the top and bottom sides 518, 520 to contain bone graft material or to serve as channels for bone growth. Each cavity 530 extends unobstructed through the spacer 512 so as to comprise a patent opening through the spacer 512. The cavities 530 are separated by two central webs 548 and encircled by an annular wall 550.

The spacer 512 has a hole 554 through the wall 550 on the trailing side 522. The hole 554 may be threaded or provided with other connection means, as described previously.

Figure 16:
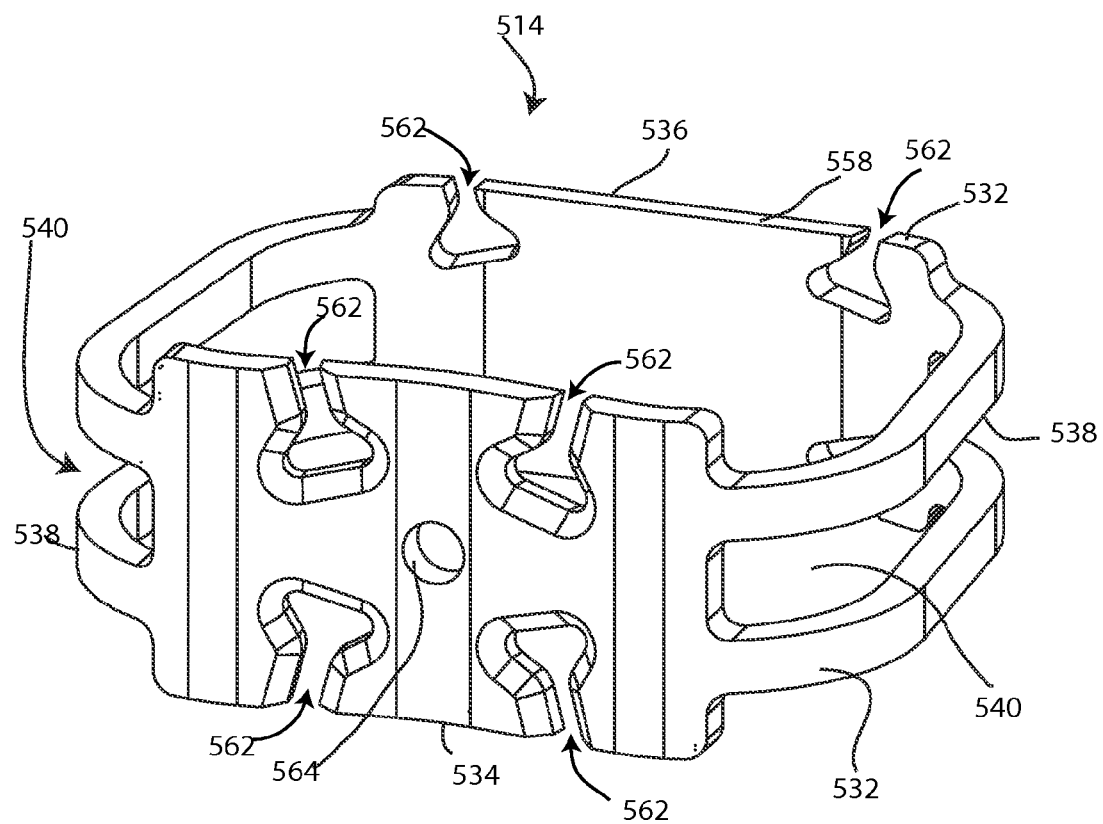
FIG. 16 is a perspective view of the jacket of FIG. 11.
Figure 17A:
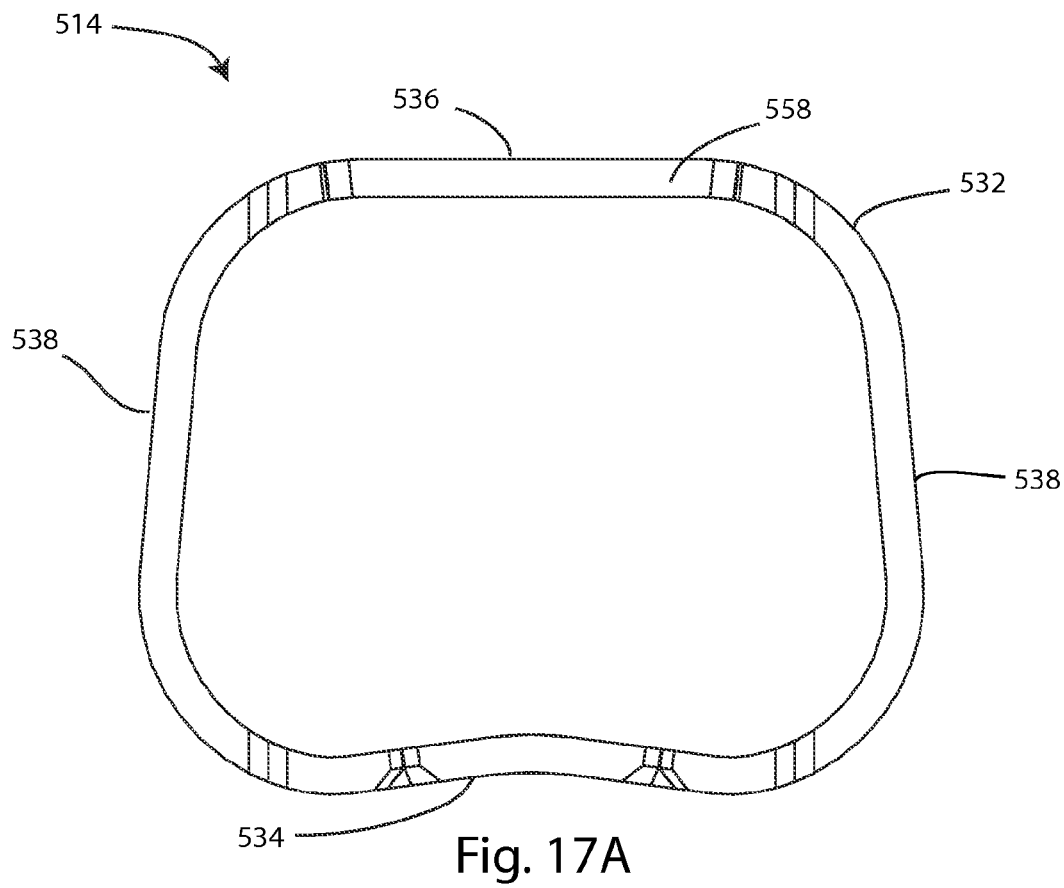
FIG. 17A is a cranial view of the jacket of FIG. 11.
Figure 17B:
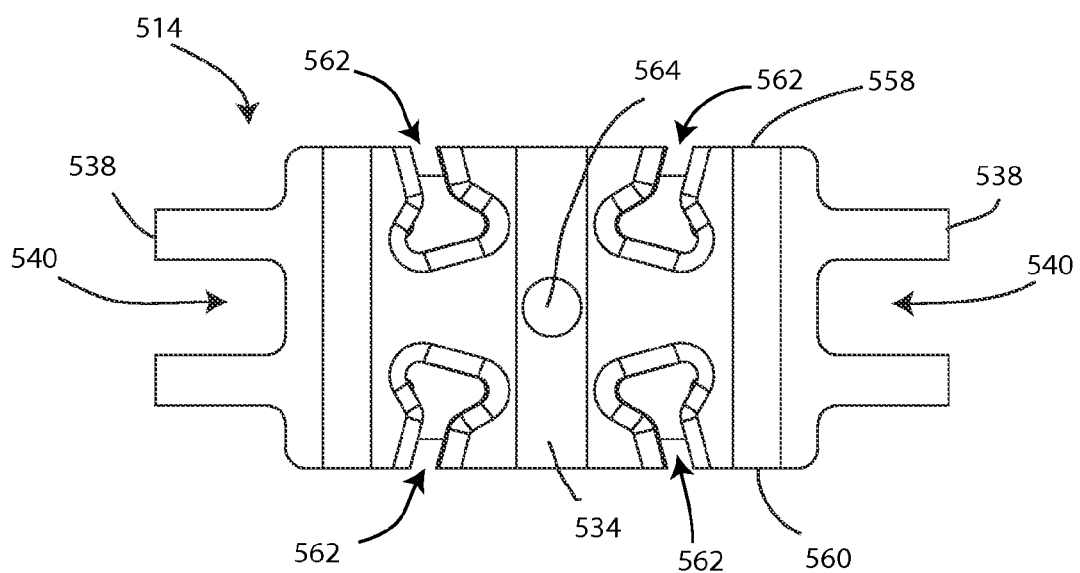
FIG. 17B is an anterior view of the jacket of FIG. 17A.

Referring to FIGS. 16-17, the jacket 514 is illustrated in a perspective view (FIG. 16), a top view (FIG. 17A) and a front view (FIG. 17B). The jacket 514 comprises an annular wall 532 extending between a top side 558 and a bottom side 560 and comprising a leading portion 536, a trailing portion 534 opposite the leading portion 536, and two side portions 538 extending between the leading 536 and trailing 534 portions. With reference to FIGS. 11-12, it can be appreciated that the leading 536 and trailing 534 portions of the jacket 514 may extend proximate the top and bottom sides 518, 520 of the spacer 512 when the spacer 512 and jacket 514 are assembled together. However, the side portions 538 may be spaced apart from the top and bottom sides 518, 520. The jacket 514 (FIG. 17A) corresponds closely to the shape of the spacer 512 (FIG. 15A) in the top view.

The jacket 514 comprises four dovetail slots 562 between the leading and trailing portions 536, 534, as shown most clearly in FIG. 16. Two dovetail slots 562 extend across the top side 558 and two dovetail slots 562 extend across the bottom side 560. The dovetail slots 562 are oriented at a compound acute relative angle as described previously for the spacer 512.

The jacket 514 has a window 540 through the side portions 538. The window 540 extends unobstructed through the jacket 514 so as to comprise a patent opening across the jacket 514.

The jacket 514 has a hole 564 through the wall 532 on the trailing portion 534. The hole 564 may be threaded or provided with other connection means, as described previously Referring to FIGS. 14 and 16, the jacket 514 is sized and shaped to fit snugly over an outer perimeter surface 542 of the spacer 512 so that the spacer 512 and jacket 514 form a spacer assembly 544, shown in FIG. 11. When the spacer 512 and the jacket 514 are assembled, the leading portion 536 of the jacket 514 is adjacent to the leading side 524 of the spacer 512, the trailing portion 534 of the jacket 514 is adjacent to the trailing side 522 of the spacer 512, the side portions 538 of the jacket 514 are adjacent to the lateral sides 526 of the spacer 512, the top side 558 of the jacket 514 is proximate the top side 518 of the spacer 512, and the bottom side 560 of the jacket 514 is proximate the bottom side 520 of the spacer 512. In this case, the ridge 528 on the spacer 512 may abut a side portion 538 of the jacket 514 when the spacer 512 and jacket 514 are assembled.

With reference to FIG. 11, the dovetail slots 546 on the top side 518 of the spacer 512 align with the dovetail slots 562 on the top side 558 of the jacket 514 to form continuous collinear interconnection features when the spacer 512 and the jacket 514 are assembled together. Similarly, the dovetail slots 546 on the bottom side 520 of the spacer 512 align with the dovetail slots 562 on the bottom side 560 of the jacket 514 to form continuous collinear interconnection features when the spacer 512 and the jacket 514 are assembled together.

The interconnection features on the spacer assembly 544 may be configured in many alternative embodiments. Considering a top side of the spacer assembly 544, there may be one or more interconnection features distributed symmetrically or asymmetrically across the spacer assembly 544. The interconnection features may be oriented parallel to each other, or at an acute angle in one or more planes of reference. Considering the top and bottom sides of the spacer assembly 544, the number of interconnection features may be equal or unequal. It can be appreciated that the number, distribution, and orientation of interconnection features on the spacer assembly 544 will correspond at least in part to the number, distribution, and orientation of anchors 516 present in prosthesis 510.

By orienting the anchors 516 at an acute relative angle in one or more planes, the prosthesis 510 may experience less post-operative migration. The compound acute relative angle discussed previously may also minimize the risk of bone fracture due to multiple stress risers created by inserting the anchors 516 into the bone.

Referring to FIGS. 11-12, the anchor 516 may be similar in design and construction to anchor 116 described previously.

Figure 18:
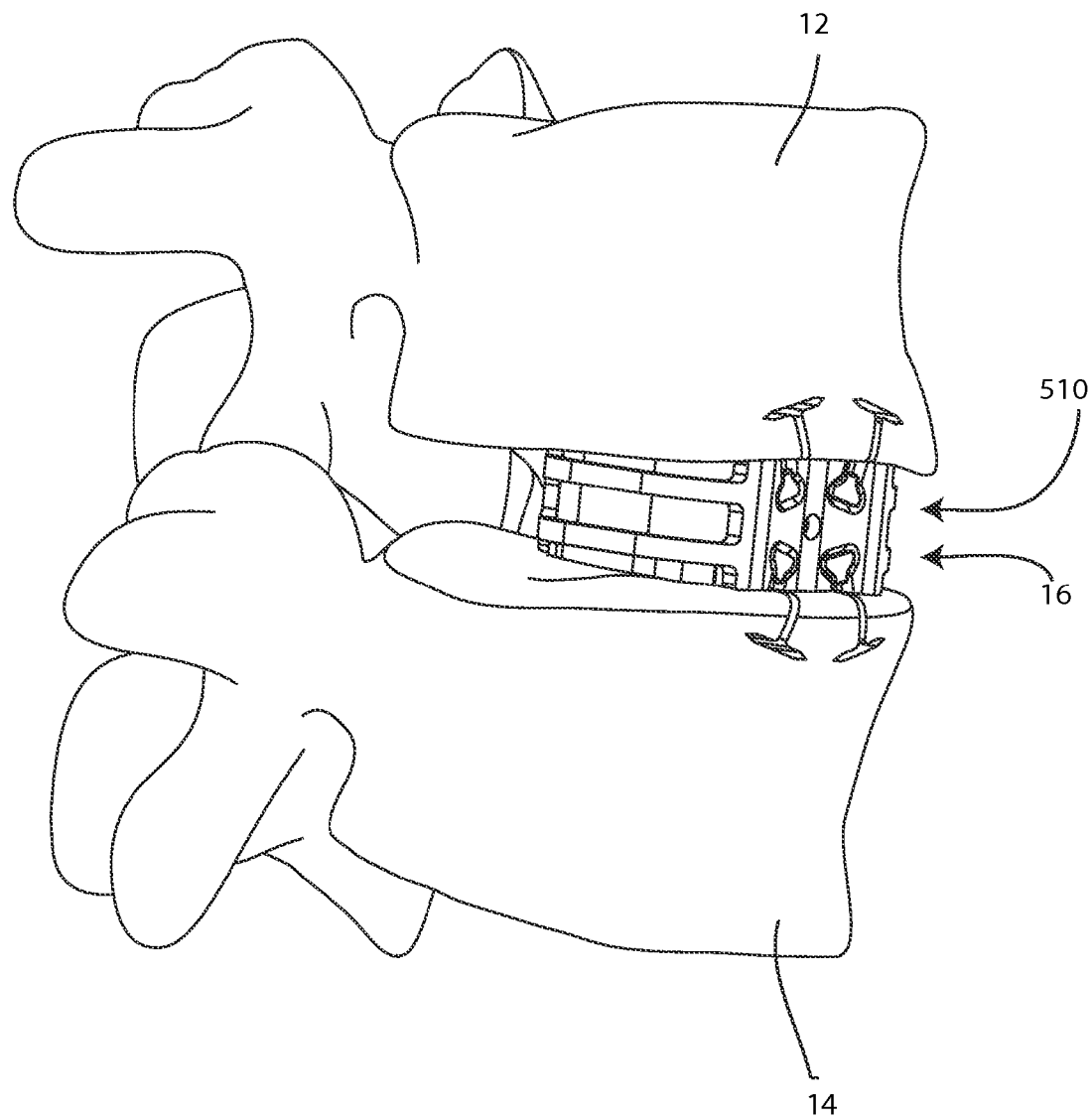
FIG. 18 is a perspective view of the intervertebral fusion prosthesis of FIG. 11, implanted in an intervertebral space between two adjacent lumbar vertebrae.

Referring to FIG. 18, the prosthesis 510 is shown implanted in an intervertebral space 16 between adjacent lumbar vertebrae 12, 14. It can be appreciated that the spacer 512 of prosthesis 510 may be sized and shaped to at least partially fill an intervertebral disc space between adjacent vertebrae at any level of the spine after removal of at least a portion of an intervertebral disc.

The method of implanting prosthesis 510 from an anterior approach is similar to that described previously for prosthesis 110. However, two anchors 516 are inserted into each adjacent vertebral body of vertebrae 12, 14, so that prosthesis 510 comprises a total of four anchors 516 when fully implanted. Because the anchors 516 are inserted in line with the dovetail slots 562, 546, the anchors 516 may be inserted at an angle to the approach used to insert the spacer assembly 544.

Figure 20A:
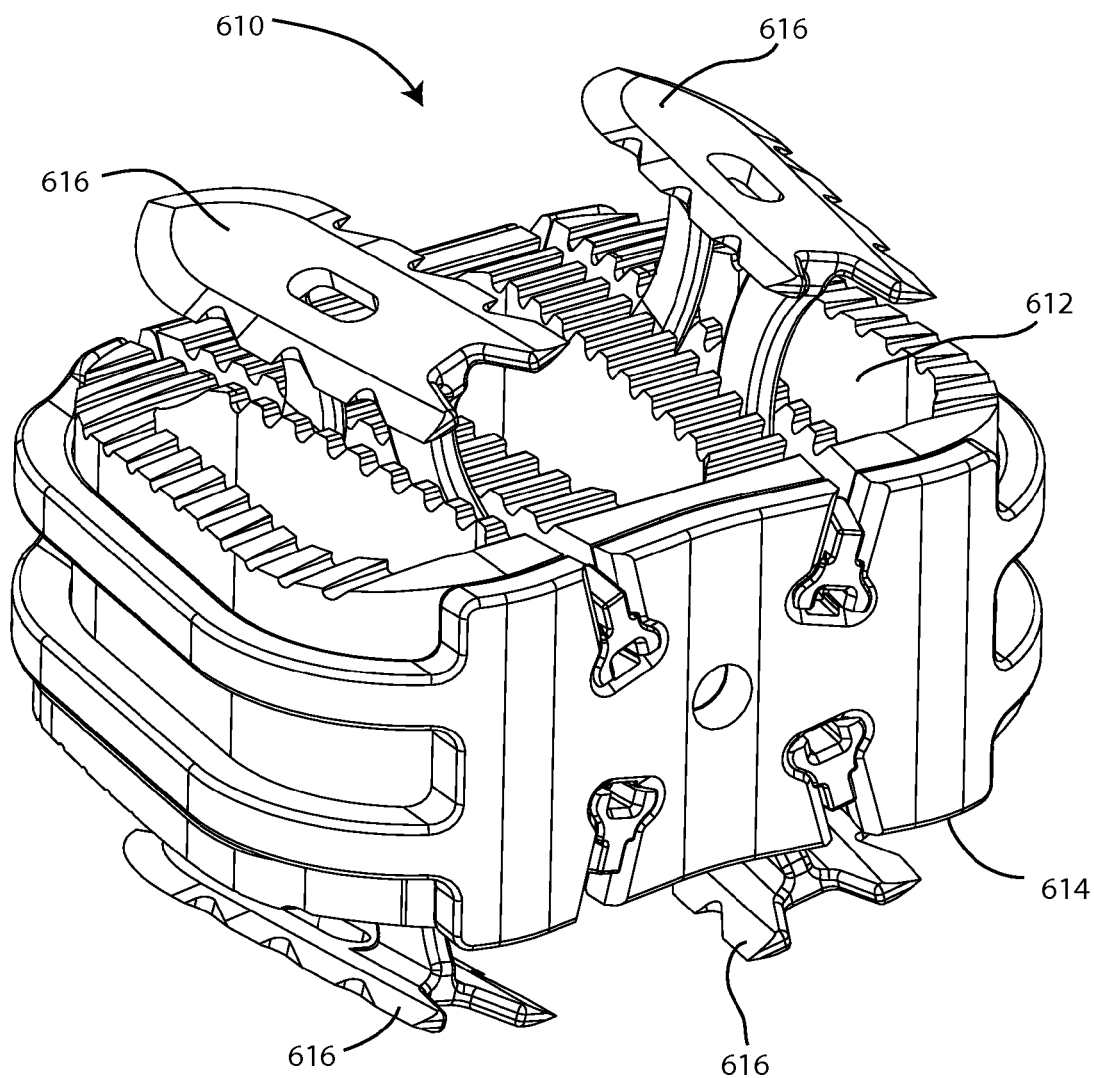
FIG. 20A is an anterior perspective view of an alternate embodiment of an intervertebral fusion prosthesis.
Figure 20B:
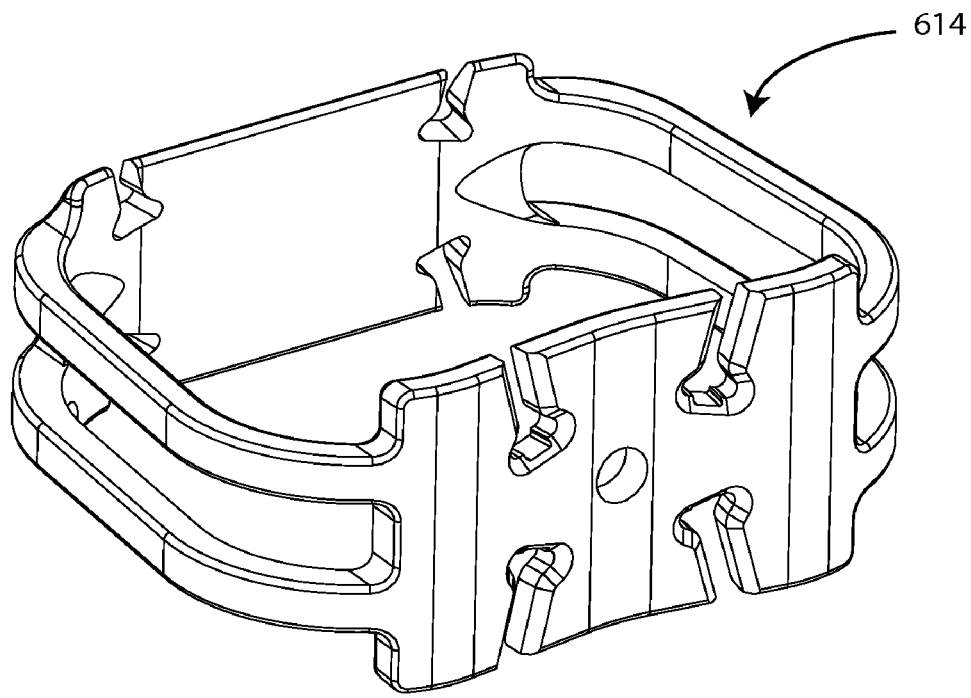
FIG. 20B is an anterior perspective view of the jacket of FIG. 20A.
Figure 20C:
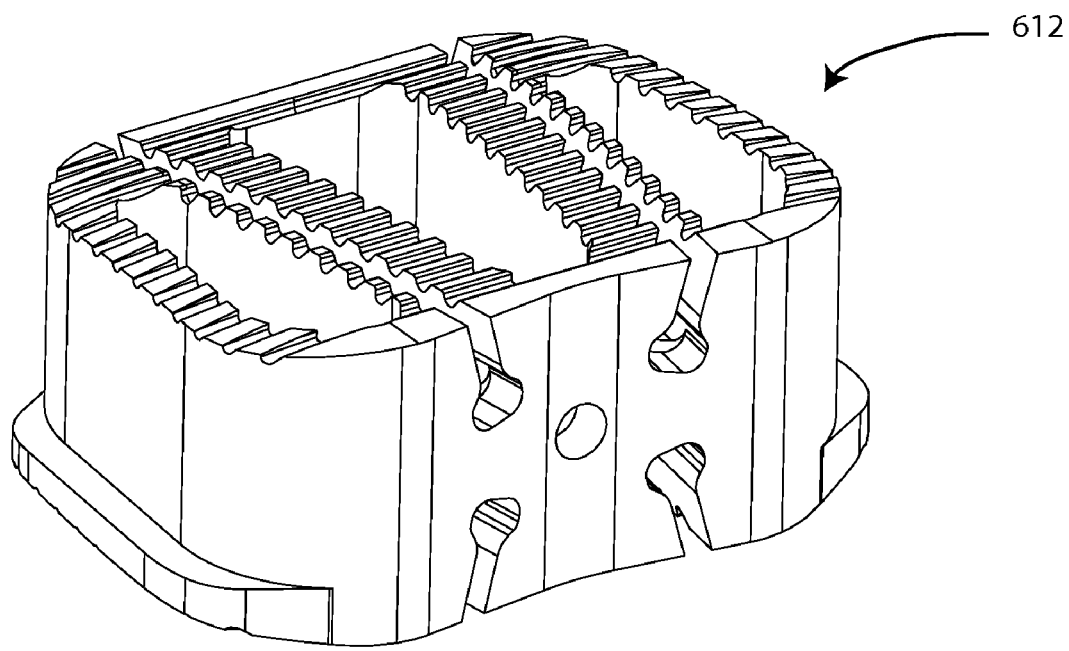
FIG. 20C is an anterior perspective view of the spacer of FIG. 20A.
Figure 20:
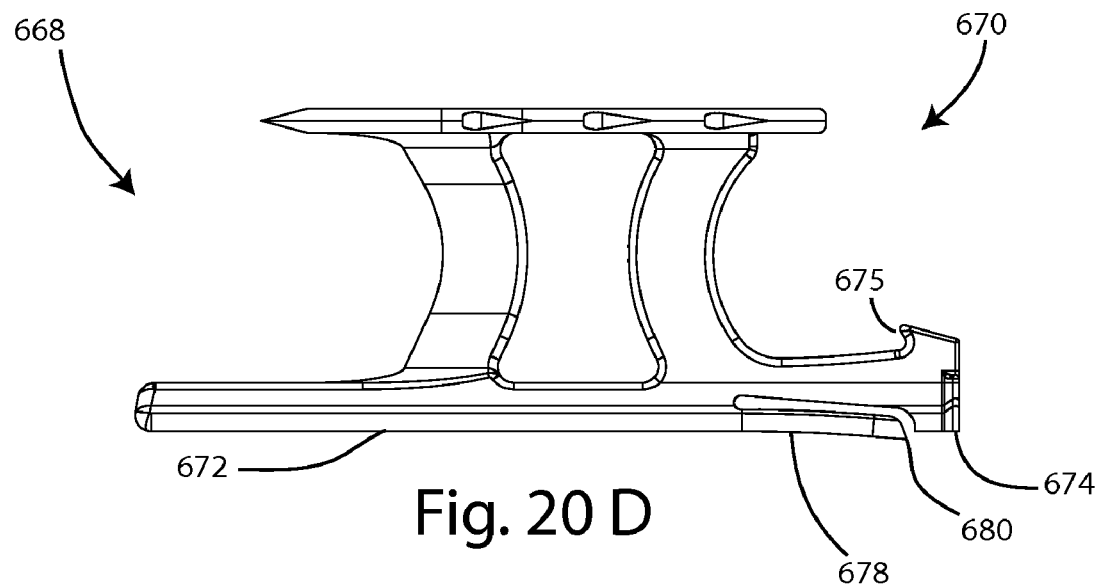
FIG. 20D is a lateral view of the anchor of FIG. 20A.
FIG. 20E is an anterior perspective view of the anchor of FIG. 20A.
Figure 20:
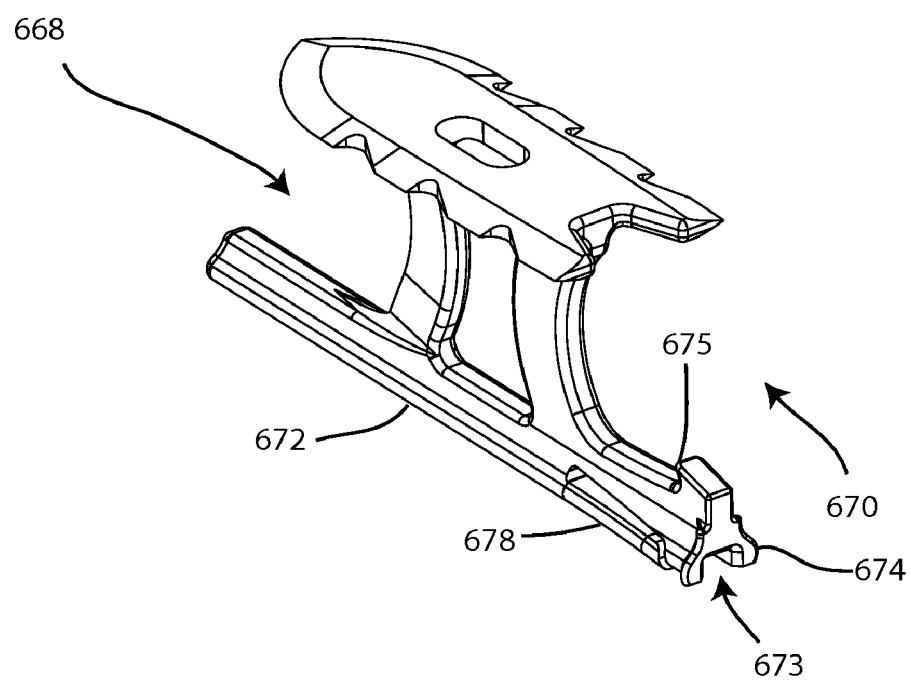

Referring to FIGS. 19-20, an alternate embodiment of an intervertebral fusion prosthesis 610 is illustrated. The prosthesis 610 comprises a spacer 612, a jacket 614, and four anchors 616.

Referring to FIG. 20B-20C, the spacer 612 and jacket 614 are illustrated.

Referring to FIG. 20D-20E, the anchor 616 is illustrated. The anchor 616 is distinguished from the previously disclosed anchor 116 in the configuration of the stop feature and locking feature. The anchor 616 also comprises a channel 673 and a hook 675 not previously disclosed for anchor 116.

The anchor 616 is generally elongate with a leading end 668 and a trailing end 670 opposite the leading end 668. The stop feature comprises a flange 674 integral to a dovetail beam 672 at the trailing end 670, similar to the description of anchor 116. The flange 674 is notched by a channel 673 extending along the dovetail beam 672. The flange 674 is also enlarged into a hook 675 disposed opposite the channel 673 on the dovetail beam 672 and opening toward the leading end 668. The locking feature comprises a flexible tab 678 integrated on the dovetail beam 672 proximate the trailing end 670 and disposed on the same side of the dovetail beam as the channel 673. This embodiment provides the same stop and lock functions described previously for the anchor 116, and provides for unlocking and removing the anchor 616 by inserting an object into the channel 673 to depress the tab 678 against the dovetail beam 672 and grasping the hook 675 to remove the anchor 616.

Figure 21A:
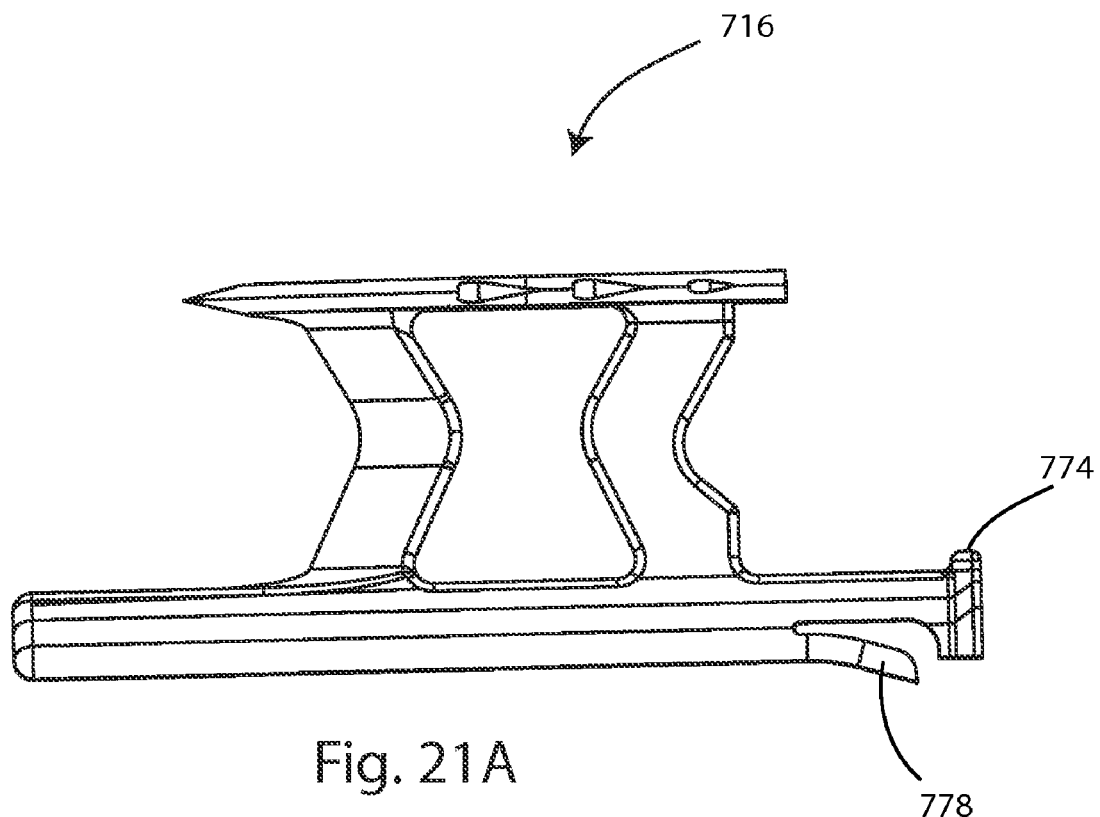
FIG. 21A (BAE-5 PROV) is a lateral view of an alternate embodiment of an anchor.
Figure 21B:
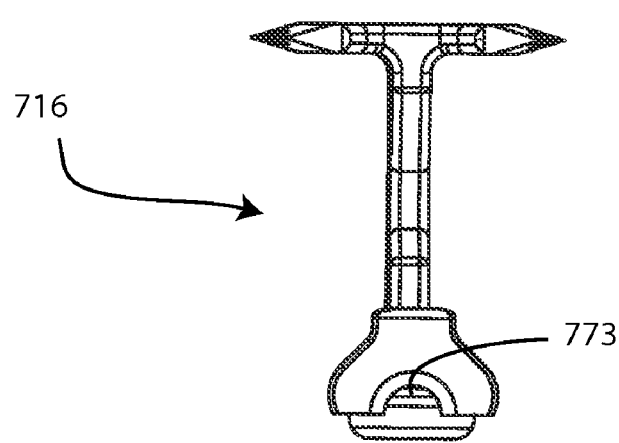
FIG. 21B is an anterior (or proximal) view of the anchor of FIG. 21A.

Referring to FIG. 21, an alternate embodiment of an anchor 716 is shown. Anchor 716 comprises a flange 774 similar to flange 174 of anchor 116, a tab 778 similar to tab 678 of anchor 616, and a channel 773 similar to channel 673 of anchor 616.

Referring to FIG. 22A-22M, various alternative embodiments are shown of an intervertebral fusion prosthesis with four anchors.

Figure 22A:
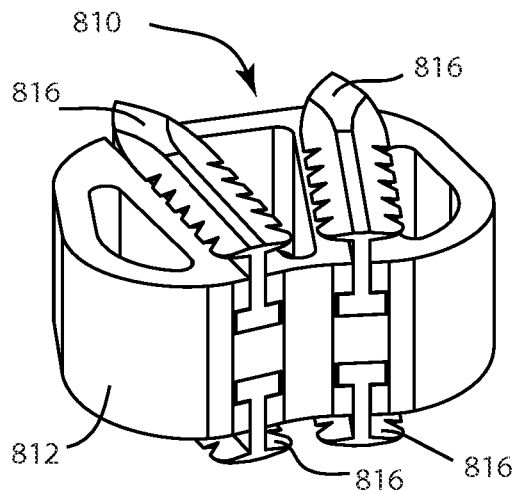
FIG. 22A is a perspective view of an alternate embodiment of an intervertebral fusion prosthesis.

Referring to FIG. 22A, an alternative embodiment of an intervertebral fusion prosthesis 810 is illustrated. Prosthesis 810 comprises a spacer 812 and four anchors 816. Prosthesis 810 comprises a T-shaped interconnection between spacer 812 and anchor 816. The anchors 816 are at an acute relative angle in only one plane.

Figure 22B:
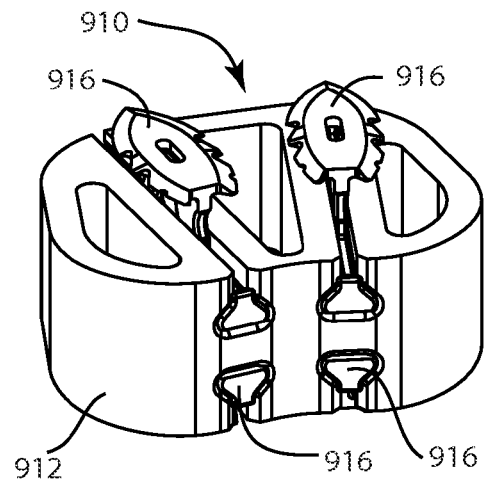
FIG. 22B is a perspective view of another alternate embodiment of an intervertebral fusion prosthesis.

Referring to FIG. 22B, another alternative embodiment of an intervertebral fusion prosthesis 910 is illustrated. Prosthesis 910 comprises spacer 912 and four anchors 916. Prosthesis 910 comprises a dovetail interconnection between spacer 912 and anchor 916. The anchors 916 are at an acute relative angle in only one plane.

Figure 22C:
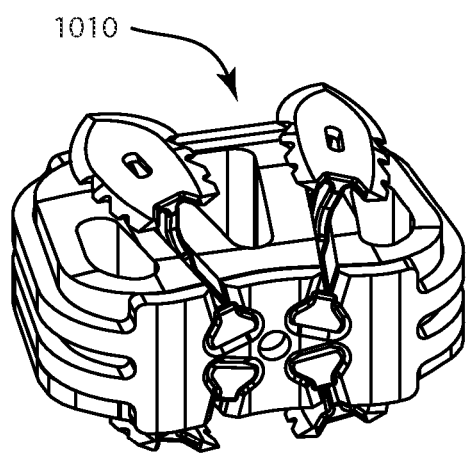
FIG. 22C is a perspective view of yet another alternate embodiment of an intervertebral fusion prosthesis.

Referring to FIG. 22C, yet another alternative embodiment of an intervertebral fusion prosthesis 1010 is illustrated.

Figure 22D:
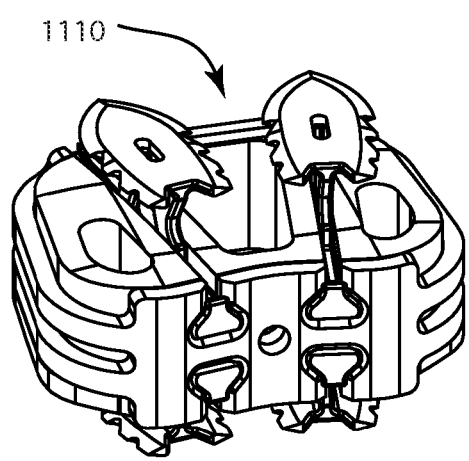
FIG. 22D is a perspective view of yet another alternate embodiment of an intervertebral fusion prosthesis.

Referring to FIG. 22D, yet another alternative embodiment of an intervertebral fusion prosthesis 1110 is illustrated.

Figure 22E:
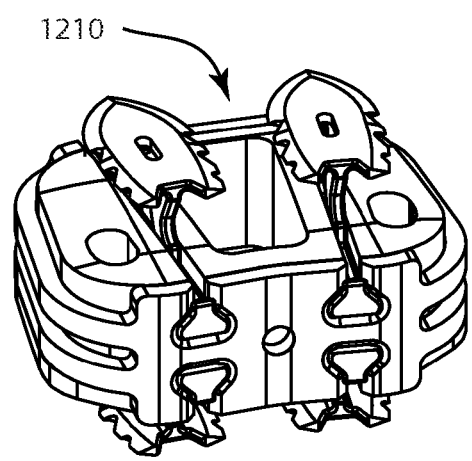
FIG. 22E is a perspective view of yet another alternate embodiment of an intervertebral fusion prosthesis.

Referring to FIG. 22E, yet another alternative embodiment of an intervertebral fusion prosthesis 1210 is illustrated.

Figure 22F:
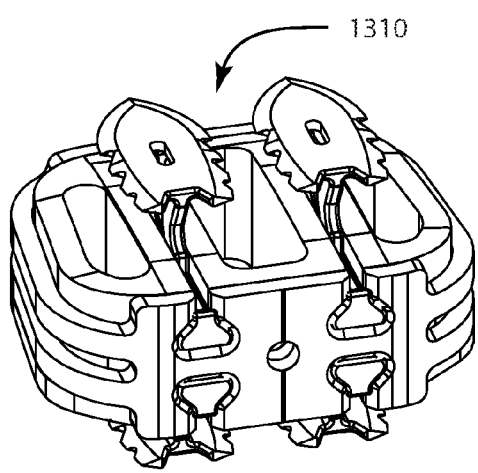
FIG. 22F is a perspective view of yet another alternate embodiment of an intervertebral fusion prosthesis.

Referring to FIG. 22F, yet another alternative embodiment of an intervertebral fusion prosthesis 1310 is illustrated.

Figure 22G:
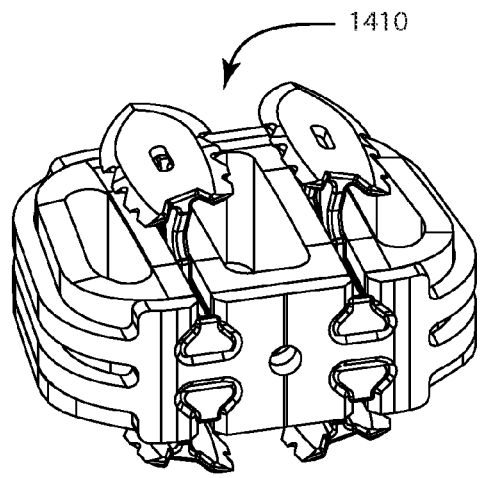
FIG. 22G is a perspective view of yet another alternate embodiment of an intervertebral fusion prosthesis.

Referring to FIG. 22G, yet another alternative embodiment of an intervertebral fusion prosthesis 1410 is illustrated.

Figure 22H:
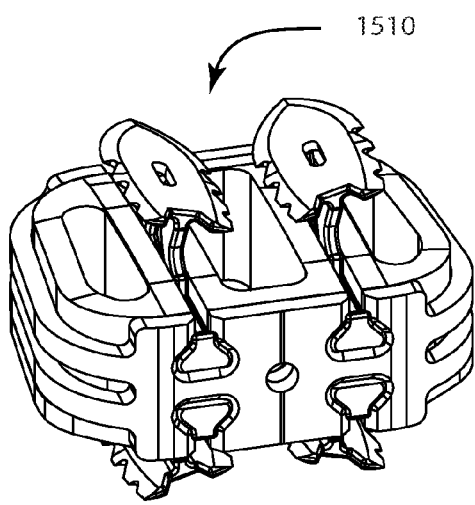
FIG. 22H is a perspective view of yet another alternate embodiment of an intervertebral fusion prosthesis.

Referring to FIG. 22H, yet another alternative embodiment of an intervertebral fusion prosthesis 1510 is illustrated.

Figure 22I:
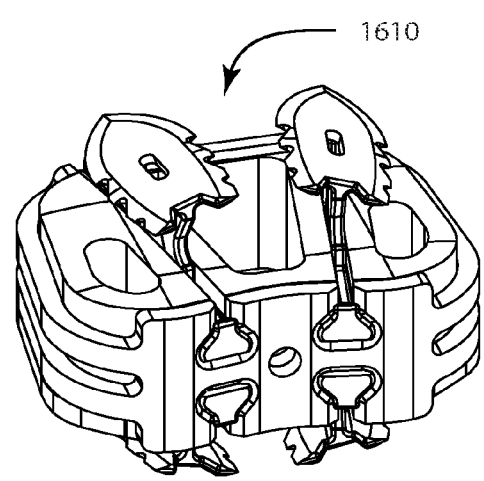
FIG. 22I is a perspective view of yet another alternate embodiment of an intervertebral fusion prosthesis.

Referring to FIG. 22I, yet another alternative embodiment of an intervertebral fusion prosthesis 1610 is illustrated.

Figure 22J:
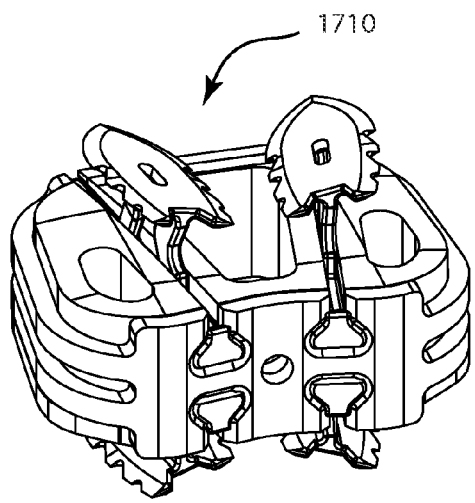
FIG. 22J is a perspective view of yet another alternate embodiment of an intervertebral fusion prosthesis.

Referring to FIG. 22J, yet another alternative embodiment of an intervertebral fusion prosthesis 1710 is illustrated.

Figure 22K:
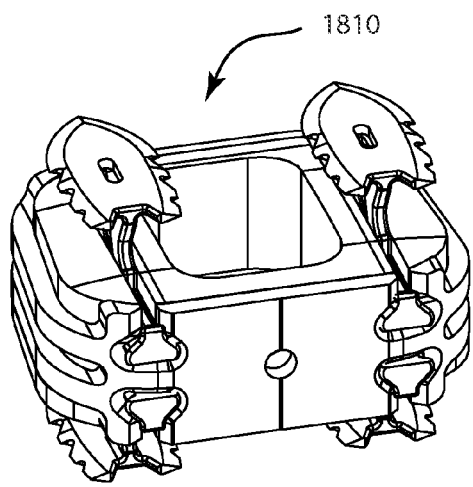
FIG. 22K is a perspective view of yet another alternate embodiment of an intervertebral fusion prosthesis.

Referring to FIG. 22K, yet another alternative embodiment of an intervertebral fusion prosthesis 1810 is illustrated.

Figure 22L:
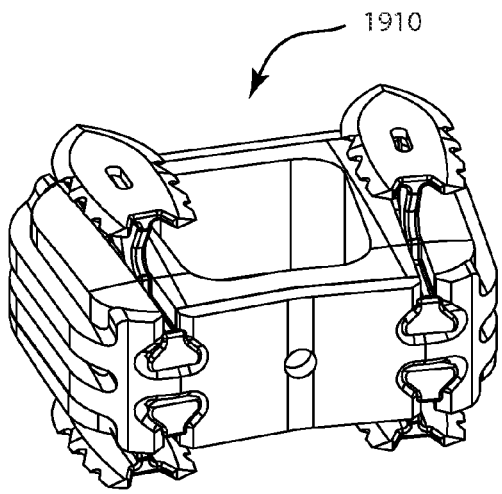
FIG. 22L is a perspective view of yet another alternate embodiment of an intervertebral fusion prosthesis.

Referring to FIG. 22L, yet another alternative embodiment of an intervertebral fusion prosthesis 1910 is illustrated.

Figure 22M:
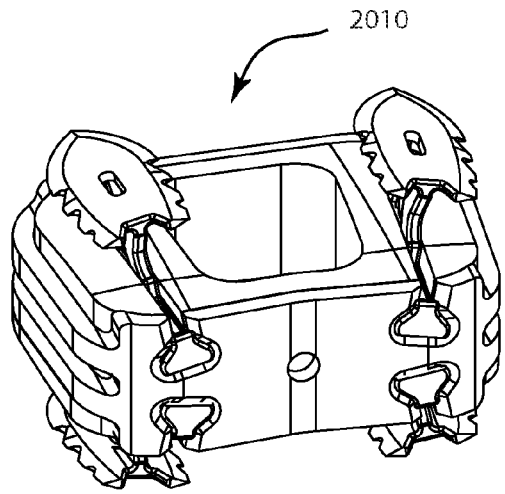
FIG. 22M is a perspective view of yet another alternate embodiment of an intervertebral fusion prosthesis.

Referring to FIG. 22M, yet another alternative embodiment of an intervertebral fusion prosthesis 2010 is illustrated.

Figure 23A:
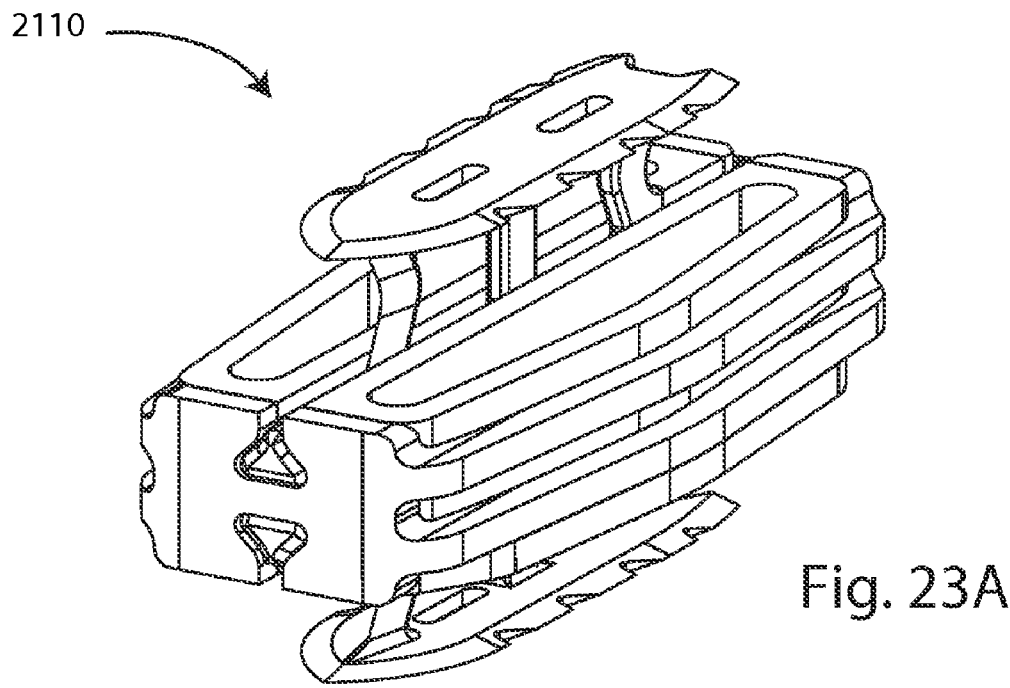
FIG. 23A is a perspective view of an alternate embodiment of an intervertebral fusion prosthesis sized and shaped to be inserted in one lateral side of an intervertebral space, comprising a spacer, a jacket and two anchors.

Referring to FIG. 23A, an alternate embodiment of an intervertebral fusion prosthesis 2110 is illustrated. Prosthesis 2110 resembles an elongated version of prosthesis 110. Prosthesis 2110 may be configured to fit in one of a right or left lateral side of an intervertebral disc space. Alternatively, prosthesis 2110 may be configured to extend laterally across an intervertebral disc space.

Figure 23B:
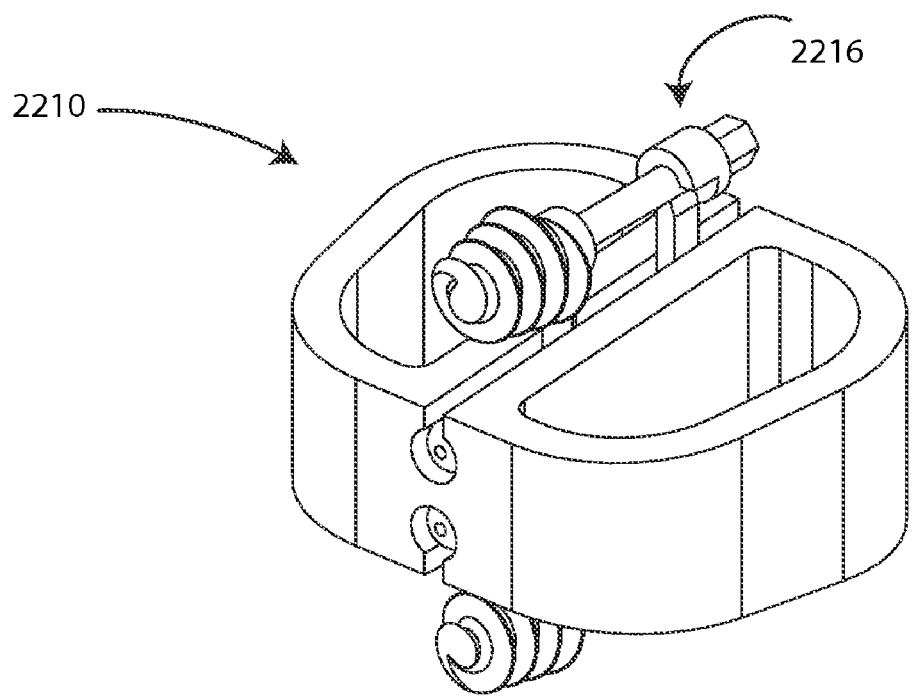
FIG. 23B is a perspective view of an alternate embodiment of an intervertebral fusion prosthesis, comprising a spacer and two screw-type anchors.

Referring to FIG. 23B, an alternate embodiment of an intervertebral fusion prosthesis 2210 is shown. Prosthesis 2210 comprises a spacer 2212 and two anchors 2216. Prosthesis 2210 comprises a keyhole-shaped interconnection between spacer 912 and anchor 916. The anchors 2216 slidingly engage the spacer 2212 and thread into adjacent bone.

One way to view the teachings set forth above is to characterize certain structures as an intervertebral spacer means for at least partially filling an intervertebral disc space between adjacent vertebrae after removal of at least a portion of an intervertebral disc. In the various embodiments set forth above, the spacers 112, 212, 512, 612, 812, 912, and 2212 as shown in FIGS. 1-3, 5, 7-8, 11-15, 18-20, and 22-23 can be characterized as intervertebral spacer means.

Certain aspects of the teachings set forth above can be characterized as jacket means for sustaining spinal loads across opposite sides of the spacer means. In the various embodiments set forth above, the jackets 114, 214, 514, and 614, as shown in FIGS. 1-2, 4-5, 7-8, 11-13, and 16-20 can be characterized as jacket means.

Certain aspects of the teachings set forth above can be characterized as anchor means for securing the spacer means to adjacent vertebrae so that the vertebrae are substantially relatively immobilized against opposite spinal motions. In the various embodiments set forth above, the anchors 116, 216, 316, 416, 516, 616, 716, 816, 916, and 2216, as shown in FIGS. 1-2, 6-13, and 18-23 can be characterized as anchor means.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for spinal fusion, comprising:
an intervertebral spacer sized and shaped to at least partially fill an intervertebral disc space between first and second adjacent vertebrae after removal of at least a portion of an intervertebral disc;
a first anchor secured to the spacer, wherein the first anchor is sized and shaped to secure the spacer to the first vertebra so that the spacer and the first vertebrae are substantially relatively immobilized against antagonistic spinal motions; and
a jacket secured around the spacer and secured to the first anchor for sustaining spinal loads across opposite sides of the spacer.

2. The system of claim 1, wherein the spacer is at least partially radiolucent.

3. The system of claim 1, wherein the first anchor is releasably secured to the jacket.

4. The system of claim 1, wherein the anchor and the jacket are metal.

5. The system of claim 1, wherein the spacer comprises a top side and a bottom side opposite the top side, wherein the first anchor extends from the top side of the spacer, wherein the system comprises a second anchor extending from the bottom side of the spacer.

6. The system of claim 5, wherein a patent opening extends through the spacer from the top side to the bottom side.

7. The system of claim 5, wherein the system comprises third and fourth anchors, wherein the third anchor extends from the top side of the spacer, and the fourth anchor extends from the bottom side of the spacer.

8. The system of claim 7, wherein each anchor comprises an interconnection portion to engage the spacer, wherein a first angle between the interconnection portions of the first and third anchors is acute in a first plane generally parallel to the top side of the spacer.

9. The system of claim 8, wherein each anchor comprises a leg extending generally perpendicular to the interconnection portion, wherein a second angle between the legs of the anchors on the top side of the spacer is acute in a second plane perpendicular to the first plane.

10. The system of claim 1,
wherein the jacket rigidly encircles the spacer,
the system further comprising a first interconnection feature extending across the spacer and the jacket,
wherein the first anchor comprises an interconnection portion, an enlarged fixation portion spaced apart from the interconnection portion, and a leg which extends between the interconnection portion and the fixation portion, wherein the first anchor comprises a rigid material,
wherein the interconnection portion of the anchor is slidably engageable with the interconnection feature extending across the spacer and the jacket, so that when the interconnection portion is engaged with the interconnection feature the anchor is rigidly secured to opposite sides of the jacket, and the fixation portion and at least a portion of the leg extend away from the spacer.

11. The system of claim 10, wherein the first interconnection feature comprises collinear dovetail grooves in the spacer and the jacket.

12. The system of claim 10, wherein the leg comprises a cutting edge on a leading end thereof, wherein the cutting edge is shaped to penetrate bone when urged against the bone.

13. The system of claim 10, wherein the anchor comprises a plurality of legs.

14. The system of claim 10,
wherein the spacer comprises a top side, a bottom side opposite the top side, a leading side, a trailing side opposite the leading side, and two lateral sides extending between the leading and trailing sides,
wherein the jacket comprises an annular wall comprising a leading portion, a trailing portion opposite the leading portion, and two side portions extending between the leading and trailing portions,
wherein the leading, trailing, and side portions of the jacket are adjacent to the respective leading, trailing, and lateral sides of the spacer,
wherein the leading and trailing portions of the jacket extend proximate the top and bottom sides of the spacer.

15. The system of claim 14, wherein each side portion of the jacket wall is spaced apart from the top and bottom sides of the spacer, wherein a patent opening extends across the jacket through the side portions.

16. The system of claim 14, wherein the first interconnection feature extends along the top side of the spacer between the leading and trailing portions of the jacket, the system further comprising a second interconnection feature that extends along the bottom side of the spacer between the leading and trailing portions of the jacket to slidably engage a second anchor.

17. The system of claim 16, further comprising a third interconnection feature that extends along the top side of the spacer between the leading and trailing portions of the jacket and a fourth interconnection feature that extends along the bottom side of the spacer between the leading and trailing portions of the jacket to respectively slidably engage third and fourth anchors.

18. The system of claim 17, wherein a first angle between the first and third interconnection features is acute in a first plane generally parallel to the top side of the spacer.

19. The system of claim 18, further comprising a third anchor having a leg, wherein when the first and third anchors are engaged within the respective first and third interconnection features, a second angle between the legs of the first and third anchors is acute in a second plane perpendicular to the first plane.

20. The system of claim 10, wherein the anchor comprises a leading end and a trailing end opposite the leading end, wherein the interconnection portion and the fixation portion each extend between the leading and trailing ends, wherein the fixation portion comprises a foliate plate oriented with a broad side of the plate facing the interconnection portion.

21. The system of claim 20, wherein the interconnection portion comprises an enlarged tip at the trailing end and a locking feature proximate the trailing end.

22. The system of claim 21, wherein the locking feature comprises a tab projecting obliquely from the interconnection portion toward the trailing end, wherein, when the anchor is secured to the jacket, the enlarged tip abuts the jacket and the tab snaps into engagement with the jacket.

23. The system of claim 20, wherein the fixation portion comprises a cutting edge proximate the leading end, wherein the cutting edge is shaped to penetrate bone when urged against the bone, wherein the fixation portion comprises a blunt profile proximate the trailing end, wherein the blunt profile is shaped to resist migration when urged against the bone.

24. The system of claim 23, wherein the fixation portion is biased to lift away from the interconnection portion as the interconnection portion slidably engages the interconnection feature and the fixation portion penetrates the bone.

25. A system for spinal fusion, comprising:
intervertebral spacer means for at least partially filling an intervertebral disc space between first and second adjacent vertebrae after removal of at least a portion of an intervertebral disc;
anchor means for securing the spacer means to a first vertebra so that the spacer means and the first vertebra are substantially relatively immobilized against opposite spinal motions; and
jacket means secured around the spacer means and secured to the anchor means for sustaining spinal loads across opposite sides of the spacer means.

26. The system of claim 25, wherein the anchor means compresses the first vertebra against the spacer means when the spacer means is secured to the first vertebra.

27. The system of claim 25, wherein the anchor means is securable to the spacer means when the spacer means at least partially fills the intervertebral disc space.

28. The system of claim 25, wherein the anchor means comprises a plurality of anchor components each disposed between the spacer and one of the first and second vertebrae.

29. The system of claim 25, wherein the anchor means and the jacket means substantially relatively immobilize the vertebrae by providing a pair of continuous rigid load paths between the vertebrae.

* * * * *